(12) United States Patent
Gubler et al.

(10) Patent No.: US 11,105,794 B2
(45) Date of Patent: Aug. 31, 2021

(54) IN VITRO NEPHROTOXICITY SCREENING ASSAY

(71) Applicant: Hoffmann-La Roche Inc., Little Falls, NJ (US)

(72) Inventors: Marcel Gubler, Arlesheim (CH); Sabine Sewing, Basel (CH); Annie Moisan, Basel (CH); Adrian B. Roth, Riehen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/310,543

(22) PCT Filed: Jun. 16, 2017

(86) PCT No.: PCT/EP2017/064770
§ 371 (c)(1),
(2) Date: Dec. 17, 2018

(87) PCT Pub. No.: WO2017/216340
PCT Pub. Date: Dec. 21, 2017

(65) Prior Publication Data
US 2019/0265230 A1    Aug. 29, 2019

(30) Foreign Application Priority Data
Jun. 17, 2016 (EP) ..................... 16174996

(51) Int. Cl.
*G01N 33/50* (2006.01)
*C12Q 1/6883* (2018.01)

(52) U.S. Cl.
CPC ....... *G01N 33/5014* (2013.01); *C12Q 1/6883* (2013.01); *G01N 33/5005* (2013.01); *G01N 33/5008* (2013.01); *G01N 33/5044* (2013.01); *C12Q 2600/142* (2013.01); *C12Q 2600/158* (2013.01); *G01N 2333/485* (2013.01)

(58) Field of Classification Search
None
See application file for complete search history.

(56) References Cited

U.S. PATENT DOCUMENTS

| | | | |
|---|---|---|---|
| 5,994,517 A | 11/1999 | Ts'o et al. | |
| 7,399,845 B2 | 7/2008 | Seth et al. | |
| 8,101,348 B2 | 1/2012 | Tuschl et al. | |
| 8,349,809 B2 | 1/2013 | Brown | |
| 8,513,207 B2 | 8/2013 | Brown | |

FOREIGN PATENT DOCUMENTS

| | | | | |
|---|---|---|---|---|
| WO | WO 2001/023613 | | 4/2001 | |
| WO | WO 2004/046160 | | 6/2004 | |
| WO | WO-2006050734 A2 | * | 5/2006 | ........... C12N 15/113 |
| WO | WO 2007/031091 | | 3/2007 | |
| WO | WO 2009/067647 | | 5/2007 | |
| WO | WO 2007/112754 | | 10/2007 | |
| WO | WO 2007/134181 | | 11/2007 | |
| WO | WO 2007/146511 | | 12/2007 | |
| WO | WO 2008/113832 | | 9/2008 | |
| WO | WO 2008/131807 | | 11/2008 | |
| WO | WO 2008/150729 | | 12/2008 | |
| WO | WO 2008/154401 | | 12/2008 | |
| WO | WO 2009/006478 | | 1/2009 | |
| WO | WO 2009/043353 | | 4/2009 | |
| WO | WO 2009/090182 | | 7/2009 | |
| WO | WO 2009/100320 | | 8/2009 | |
| WO | WO 2009/124238 | | 10/2009 | |
| WO | WO 2009/124295 | | 10/2009 | |
| WO | WO 2009/126933 | | 10/2009 | |
| WO | WO 2010/036698 | | 4/2010 | |
| WO | WO 2011/017521 | | 2/2011 | |
| WO | WO 2011/085102 | | 7/2011 | |
| WO | WO 2011/115818 | | 9/2011 | |
| WO | WO 2012/083046 | | 6/2012 | |
| WO | WO 2012/089352 | | 7/2012 | |
| WO | WO 2013/154798 | | 10/2013 | |
| WO | WO 2014/118267 | | 8/2014 | |
| WO | WO 2014/179445 | | 11/2014 | |
| WO | WO 2014/179620 | | 11/2014 | |
| WO | WO-2014207232 A1 | * | 12/2014 | ........... C12N 15/113 |
| WO | WO-2016079181 A1 | * | 5/2016 | ............. C07H 21/00 |
| WO | WO-2016096938 A1 | * | 6/2016 | ........... C12N 15/113 |
| WO | WO 2017/067970 | | 4/2017 | |

OTHER PUBLICATIONS

Kim et al. "Drug-induced nephrotoxicity and its biomarkers." Biomolecules & Therapeutics 20.3 (2012): 268. (Year: 2012).*
Taira et al. "Immunochemical study of epidermal growth factor in rats with mercuric chloride-induced acute renal failure." Nephron 67.1 (1994): 88-93 (Year: 1994).*
Bruce et al, "Ex vivo culture and separation of functional renal cells," Methods Mol Biol., 2013, 1001:53-64.
Deleavey and Damha, "Designing chemically modified oligonucleotides for targeted gene silencing.," Chemistry and Biology, Aug. 24, 2012, 19(8):937-354.
Freier & Altmann, "The ups and downs of nucleic acid duplex stability: structure-stability studies on chemically-modified DNA:RNA duplexes," Nucl. Acid Res., Nov. 15, 1997, 25(22):4429-4443.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., Aug. 2009, 5:838-843.

(Continued)

*Primary Examiner* — Emily A Cordas
(74) *Attorney, Agent, or Firm* — Fish & Richardson P.C.

(57) ABSTRACT

The invention relates to methods for predicting the in vivo nephrotoxicity of a drug substance, in particular a nucleic acid molecule such as a siRNA or an antisense oligonucleotide using an in vitro cell based assay measuring the levels of extracellular EGF as toxicity biomarker, potentially in combination with other biomarkers like ATP and KIM-1.

21 Claims, 1 Drawing Sheet
Specification includes a Sequence Listing.

(56) References Cited

OTHER PUBLICATIONS

Hangeland et al., "Cell-type specific and ligand specific enhancement of cellular uptake of oligodeoxynucleoside methylphosphonates covalently linked with a neoglycopeptide, YEE(ah-GalNAc)3," Bioconjug Chem., Nov.-Dec. 1995, 6(6):695-701.

Herrington et al, "Association of long-term administration of the survivin mRNA-targeted antisense oligonucleotide LY2181308 with reversible kidney injury in a patient with metastatic melanoma," Am J Kidney Dis., Feb. 2011, 57(2):300-303.

Henry et al., "Evaluation of the toxicity of ISIS 2302, a phosphorothioate oligonucleotide, in a four-week study in cynomolgus monkeys," Toxicology, Jun. 27, 1997, 120(2):145-155.

Huang et al., "Cell-and biomarker-based assays for prediction Nephrotoxicity," Expert Opinion on Drug Metabolism & Toxicology, Nov. 10, 2014, 10(12):1621-1635.

International Search Report and Written Opinion in International Applicaition No. PCT/EP2017/064770, dated Sep. 6, 2017, 12 pages.

International Preliminary Report and Written Opinion in International Application No. PCT/EP2017/064770, dated Dec. 18, 2018, 8 pages.

Ju et al.,"Tissue transcriptome-driven identification of epidermal growth factor as a chronic Kidney disease thomarker," Science Translation Medicine, Dec. 2, 2015, 7(316):316ra193.

Langer, "New methods of drug delivery," Science, Sep. 28 1990, 249(4976):1527-1533.

Lima et al., "Single-Stranded siRNAs Activate RNAi in Animals," Cell, Aug. 31, 2012, 150(5):883-894.

Mangos et al., "Efficient RNase H-directed cleavage of RNA promoted by antisense DNA or 2'F-ANA constructs containing acyclic nucleotide inserts.," J Am Chem Soc., Jan. 22, 2003, 125(3):654-661.

Meer et al., "Renal Effects of Antisense-Mediated Inhibition of SGLT2," Nov. 2016, J Pharmacol Exp Ther., 359(2):280-289.

Monteith et al., "Evaluation of the renal effects of an antisense phosphorothioate oligodeoxynucleotide in monkeys," Toxicologic pathology, 1999, 27(3):307.

Remington's Pharmaceutical Sciences, "Preformulation," Mack Publishing Company, Philadelphia, Pa., 17th ed., 1985, pp. 1409-1423.

Rukov et al., "Dissecting the target specificity of RNase H recruiting oligonucleotides using massively parallel reporter analysis of short RNA motifs," Nucleic Acids Res., Sep. 30, 2015, 43(17):8476-8487.

Seth at al., "Synthesis and Biophysical Evaluation of 2',4'-Constrained 2' O-Methoxyethyl and 2',4'-Constrained 2' O-Ethyl Nucleic Acid Analogues," J. Org. Chem, Mar. 5, 2010, 75(5):1569-1581.

Sohn et al., "In vitro evaluation of biomarkers for cisplatin-induced nephrotoxicity using HK-2 human kidney epithelial cells," Toxicology Letters, 2013, 217(3):235-242.

Soifer et al., "Silencing of gene expression by gymnotic delivery of antisense oligonucleotides," Methods Mol Biol, 2012, 815:333-46.

Stein et al., "Efficient gene silencing by delivery of locked nucleic acid antisense oligonucleotides, unassisted by transfection reagents," Nucleic Acids Res., Jan. 2010, 38(1):e3.

Uhlmann, "Recent Advances in the Medicinal Chemistry of Antisense Oligonucleotides," Curr. Opinion in Drug Development, 2000, 3(2), 293-213).

Van Poelgeest et al.,"Antisense-mediated reduction of proprotein convertase subtilisin/kexin type 9 (PCSK9): a first-in-human randomized, placebo-controlled trial," British journal of clinical pharmacology, Dec. 2015, 80(6):1350-1361.

Vester et al., "Chemically modified oligonucleotides with efficient RNase H response," Bioorg. Med. Chem. Lett., Apr. 1, 2008, 18(7):2296-2300.

Voit et al., "Safety and efficacy of drisapersen for the treatment of Duchenne muscular dystrophy (DEMAND II): an exploratory, randomised, placebo-controlled phase 2 study," Lancet Neurology, Oct. 2014, 13:987-996.

Wan et al., "Syntesis, biophysical properties and biological activity of second generation antisense oligonucleotides containing chiral Phosphorothiate linkages," Nucleic Acids Research, Nov. 2014, 42(22):13456-13468.

Wilmer et al., "Kidney-on-a-chip Technology for Drug-Induced Nephrotocxicity Screening," Trends in Biotechnology, Feb. 2016, 34(2):156-170.

Huang et al., "Evaluation of biomarkers for in vitro prediction of drug-induced nephrotoxicity: comparison of HK-2, immortalized human proximal tubule epithelial, and primary cultures of human proximal tubular cells," Pharmacological Research & Perspectives, 2015, 3(3):e00148.

* cited by examiner

| | Target | Myd88 | Myd88 | Bcl11a | Bcl11a | Myd88 | Myd88 | Myd88 | Myd88 | Bcl11a | Bcl11a | Bcl11a | Bcl11a | Myd88 | Myd88 |
|---|---|---|---|---|---|---|---|---|---|---|---|---|---|---|---|
| | CMP ID | 6-1 | 7-1 | 18-1 | 19-1 | 9-1 | 10-1 | 11-1 | 13-1 | 15-1 | 16-1 | 19-2 | 17-1 | 12-1 | 8-1 |
| RAT | Histopath. | clean | clean | toxic | toxic | toxic | toxic | toxic | toxic | toxic | toxic | toxic | toxic | toxic | toxic |
| | Biomarker | | | | | | | | | | | | | | |
| PTEC-TERT1 | EGF | 118 | 67 | 290 | 413 | 1593 | 783 | 371 | 39 | 234 | 707 | 770 | 693 | 71 | 1545 |
| | KIM-1 | 122 | 120 | 181 | 77 | 116 | 65 | 82 | 252 | 25 | 129 | 28 | 140 | 289 | 54 |
| | ATP | 101 | 107 | 105 | 76 | 103 | 60 | 119 | 114 | 52 | 113 | 40 | 96 | 90 | 43 |

SEQUENCE LISTING

<160> NUMBER OF SEQ ID NOS: 20

<210> SEQ ID NO 1
<211> LENGTH: 16
<212> TYPE: DNA
<213> ORGANISM: Artificial
<220> FEATURE:
<223> OTHER INFORMATION: Oligonucleotide motif

<400> SEQUENCE: 1
cgtcagtatg cgaatc                                              16

<210> SEQ ID NO 2
<211> LENGTH: 16
<212> TYPE: DNA
<213> ORGANISM: Artificial
<220> FEATURE:
<223> OTHER INFORMATION: Oligonucleotide motif

<400> SEQUENCE: 2
aatgctacaa aaccca                                              16

<210> SEQ ID NO 3
<211> LENGTH: 14
<212> TYPE: DNA
<213> ORGANISM: Artificial

```
<220> FEATURE:
<223> OTHER INFORMATION: Oligonucleotide motif

<400> SEQUENCE: 3
tgctacaaaa ccca                                                       14

<210> SEQ ID NO 4
<211> LENGTH: 15
<212> TYPE: DNA
<213> ORGANISM: Artificial
<220> FEATURE:
<223> OTHER INFORMATION: Oligonucleotide motif

<400> SEQUENCE: 4
gctgtgtgag cttgg                                                      15

<210> SEQ ID NO 5
<211> LENGTH: 16
<212> TYPE: DNA
<213> ORGANISM: Artificial
<220> FEATURE:
<223> OTHER INFORMATION: Oligonucleotide motif

<400> SEQUENCE: 5
taaggcaatc aaggta                                                     16

<210> SEQ ID NO 6
<211> LENGTH: 16
<212> TYPE: DNA
<213> ORGANISM: Artificial
<220> FEATURE:
<223> OTHER INFORMATION: Oligonucleotide motif

<400> SEQUENCE: 6
caaaggaaac acacat                                                     16

<210> SEQ ID NO 7
<211> LENGTH: 16
<212> TYPE: DNA
<213> ORGANISM: Artificial
<220> FEATURE:
<223> OTHER INFORMATION: Oligonucleotide motif

<400> SEQUENCE: 7
caaatgctga aactat                                                     16

<210> SEQ ID NO 8
<211> LENGTH: 16
<212> TYPE: DNA
<213> ORGANISM: Artificial
<220> FEATURE:
<223> OTHER INFORMATION: Oligonucleotide motif

<400> SEQUENCE: 8
actgctttcc actctg                                                     16

<210> SEQ ID NO 9
<211> LENGTH: 16
<212> TYPE: DNA
<213> ORGANISM: Artificial
<220> FEATURE:
<223> OTHER INFORMATION: Oligonucleotide motif

<400> SEQUENCE: 9
gcctcccagt tcctttt                                                    16
```

```
<210> SEQ ID NO 10
<211> LENGTH: 16
<212> TYPE: DNA
<213> ORGANISM: Artificial
<220> FEATURE:
<223> OTHER INFORMATION: Oligonucleotide motif

<400> SEQUENCE: 10
cacattcctt gctctg                                                        16

<210> SEQ ID NO 11
<211> LENGTH: 14
<212> TYPE: DNA
<213> ORGANISM: Artificial
<220> FEATURE:
<223> OTHER INFORMATION: Oligonucleotide motif

<400> SEQUENCE: 11
tgctcaacat caag                                                          14

<210> SEQ ID NO 12
<211> LENGTH: 14
<212> TYPE: DNA
<213> ORGANISM: Artificial
<220> FEATURE:
<223> OTHER INFORMATION: Oligonucleotide motif

<400> SEQUENCE: 12
ttacacttga ccca                                                          14

<210> SEQ ID NO 13
<211> LENGTH: 14
<212> TYPE: DNA
<213> ORGANISM: Artificial
<220> FEATURE:
<223> OTHER INFORMATION: Oligonucleotide motif

<400> SEQUENCE: 13
tttacacttg accc                                                          14

<210> SEQ ID NO 14
<211> LENGTH: 16
<212> TYPE: DNA
<213> ORGANISM: Artificial
<220> FEATURE:
<223> OTHER INFORMATION: Oligonucleotide motif

<400> SEQUENCE: 14
gtcagaaaca accacc                                                        16

<210> SEQ ID NO 15
<211> LENGTH: 14
<212> TYPE: DNA
<213> ORGANISM: Artificial
<220> FEATURE:
<223> OTHER INFORMATION: Oligonucleotide motif

<400> SEQUENCE: 15
ctatgtgttc ctgt                                                          14

<210> SEQ ID NO 16
<211> LENGTH: 16
<212> TYPE: DNA
<213> ORGANISM: Artificial
<220> FEATURE:
<223> OTHER INFORMATION: Oligonucleotide motif
```

```
<400> SEQUENCE: 16
cgtttgtgct cgataa                                                      16

<210> SEQ ID NO 17
<211> LENGTH: 15
<212> TYPE: DNA
<213> ORGANISM: Artificial
<220> FEATURE:
<223> OTHER INFORMATION: Oligonucleotide motif

<400> SEQUENCE: 17
cgtttgtgct cgata                                                       15

<210> SEQ ID NO 18
<211> LENGTH: 16
<212> TYPE: DNA
<213> ORGANISM: Artificial
<220> FEATURE:
<223> OTHER INFORMATION: Oligonucleotide motif

<400> SEQUENCE: 18
attgcattgt ttccgt                                                      16

<210> SEQ ID NO 19
<211> LENGTH: 16
<212> TYPE: DNA
<213> ORGANISM: Artificial
<220> FEATURE:
<223> OTHER INFORMATION: Oligonucleotide motif

<400> SEQUENCE: 19
cattgcattg tttccg                                                      16

<210> SEQ ID NO 20
<211> LENGTH: 12
<212> TYPE: DNA
<213> ORGANISM: Artificial
<220> FEATURE:
<223> OTHER INFORMATION: Oligonucleotide motif

<400> SEQUENCE: 20
ggcatgagct tc                                                          12
```

IN VITRO NEPHROTOXICITY SCREENING ASSAY

CROSS REFERENCE TO RELATED APPLICATIONS

This application is a National Phase application under 35 U.S.C. § 371 of PCT International Application number PCT/EP2017/064770 filed Jun. 16, 2017, which claims priority to EP Patent Application No. 16196129.7 filed Oct. 27, 2016 and EP Patent Application No. 16174996.5 filed Jun. 17, 2016. The entire contents of the foregoing applications are hereby incorporated by reference.

FIELD OF INVENTION

The invention relates to methods for predicting the in vivo nephrotoxicity of a drug substance, in particular a nucleic acid molecule such as a siRNA or an antisense oligonucleotide using an in vitro cell based assay measuring the levels of epidermal growth factor (EGF) as toxicity biomarker, potentially in combination with other biomarkers like adenosine triphosphate (ATP) and kidney injury molecule-1 (KIM-1). The invention further relates to methods for selecting one or more drug substances for in vivo administration from a library of drug substances, in particular a nucleic acid molecule such as a RNAi agent or an antisense oligonucleotide, using said assay.

BACKGROUND

One of the issues in identification of new as well as optimized drug candidates is the event of dose limiting toxicity. When evaluated in vivo, typically a sub-set of drug substance compounds will elicit a toxicity phenotype, such as drug induced kidney injury or nephrotoxicity.

In the past few years a number of models for predicting nephrotoxicity of drug substances have been developed using various biomarkers.

Sohn et al 2013 Toxicology letters Vol 217 pp 235 and Huang et al 2015 Pharmacological Research & Perspectives Vol 3 pp e00148 both disclose in vitro cell based assays for the prediction of nephrotoxicity of small molecules using various biomarkers including kidney injury molecule-1 (KIM-1).

Ju et al 2015 Science translational medicine Vol 7, pp 316ra193 describes epidermal growth factor (EGF) as a potential in vivo biomarker for chronic kidney disease by measuring EGF transcript and secretion in the urine correlated to the glomerular filtration rate. There is no description of measuring in vitro extracellular EGF uptake.

Wilmer et al 2016 Trends in Biotechnology Vol 34 pp 156 reviews further biomarkers for screening of drug-induced nephrotoxicity both in vivo and in vitro (see table 2).

In vitro nephrotoxicity assays have shown some ability to predict known nephrotoxicity of some small molecule or polypeptide drug substances such as amphotericin B (anti-fungal agent), colistin (polypeptide antibiotic), ciclosporin (immonosupressant agent), cisplatin (chemotherapeutic agent), doxorubicin (chemotherapeutic agent), gentamicin (anti-bacterial agent).

This has however not been the case for a different class of drugs namely nucleic acid based drugs such as iRNAs, antisense oligonucleotides and aptamers. Nephrotoxicity of individual nucleic acid compounds has been published previously and appears to be unpredictable (see for example Henry et al 1997 Toxicology Vol 120 pp 145; Monteith et al 1999 Toxicologic pathology Vol 27, pp. 307; Herrington et al 2011 American journal of kidney diseases: the official journal of the National Kidney Foundation Vol 57, pp 300; Voit et al. 2014 The Lancet. Neurology Vol 13, pp 987; van Poelgeest et al 2015 British journal of clinical pharmacology Vol 80, pp 1350).

To our knowledge an in vitro cell based assay using EGF as a biomarker for the prediction of nephrotoxicity of a drug substance has not been described. In particular the in vitro prediction of nephrotoxicity of nucleic acid based molecules has not previously been described.

OBJECTIVE OF THE INVENTION

The present invention establishes EGF as a reliable biomarker in an in vitro cell based assay for prediction of in vivo nephrotoxicity of a drug compound, in particular for nucleic acid molecules, such as antisense oligonucleotides.

Reliable in vitro predictions of nephrotoxicity would increase the successful clinical development of drugs, and without the use of animals for the initial screening drug discovery will be more cost-effective, efficient and ethical, reducing the number of animals needed for toxicity screening of libraries of drug substances significantly.

SUMMARY OF THE INVENTION

The invention provides in vitro toxicity assays which have been found to be predictive for in vivo nephrotoxicity of drug substances, in particular oligonucleotides, such as antisense oligonucleotides.

In one aspect of the invention, the present inventors have identified epidermal growth factor (EGF) as a biomarker of nephrotoxicity, when the drug substance is administered to cells expressing epidermal growth factor receptor (EGFR). The EGF biomarker can be combined with other biomarkers such as adenosine triphosphate (ATP), and/or kidney injury molecule-1 (KIM-1).

The invention provides for an in vitro method (an assay) for predicting in vivo toxicity (or in vivo toxicity potential) which may be used to select drug substance compounds which are, or are predicted to be, suitable for in vivo administration without adverse nephrotoxicity, such as acute kidney injury or drug-induced kidney injury.

The invention provides for a method for predicting the in vivo nephrotoxicity of a drug substance, in particular a nucleic acid based molecule such as an antisense oligonucleotide in a mammal, said method comprising the steps of:

a. culturing cells expressing epidermal growth factor receptor (EGFR) in a suitable cell culture media containing at least 4 ng/ml of epidermal growth factor (EGF);
b. administering the drug substance to said cell culture;
c. incubating the cells for a period of time; and
d. subsequently measuring the EGF level in the supernatant;

wherein an increase in EGF in the supernatant is indicative of a drug substance which is, or is predicted to be, associated with nephrotoxicity.

The invention provides for a method for selecting one or more drug substances suitable for in vivo administration, from a library of drug substances, said method comprising the steps of a. obtaining a library of drug substances;
b. administering each member of the library of drug substances to cell culture expressing epidermal growth factor receptor (EGFR) and where the medium contains at least 4 ng/ml of epidermal growth factor (EGF);

c. culturing the cells in vitro for a period of time;

d. measuring the amount of extracellular EGF for each drug substance; and e. selecting one or more drug substances wherein the toxicity grade is below 6.

Optionally, the methods may further comprise the step of administering the selected drug substance in vivo to a mammal.

Suitably, in the methods of the invention the level or amount of the at least one biomarker may be compared to the level obtained when administering a non-toxic reference drug substance (confirmed as non-toxic in vivo) to determine the level of increase or decrease of the at least one biomarker due to the administration of the drug substance (i.e. an alteration of the at least one biomarker of nephrotoxicity). Furthermore, the at least one biomarker may be compared to the level obtained when administering a toxic reference drug substance (confirmed as toxic in vivo) to determine the assay window of the at least one biomarker.

In some embodiments the cells expressing EGFR is selected from cell cultures originating from epithelial cells, mesenchymal cells, neuroectodermal cells and hepatocytes. In particular cell cultures originating from kidney epithelial cells are useful in the methods of the inventions, such as human PTEC or human PTEC-TERT-1 cell cultures.

In some embodiments, the predicted nephrotoxicity is associated with an increase of EGF as a biomarker in the cell culture media. In further embodiments an increase in KIM-1 levels are indicative of a drug substance which is, or is predicted to be, associated with nephrotoxicity. Further biomarkers for predicting nephrotoxicity may be associated with a decrease in intracellular ATP levels. The invention provides for the use of an in vitro assay to determine the (e.g. likely) nephrotoxicity of a drug substance, in particular a nucleic acid based molecule, such as an oligonucleotide, such as a LNA oligonucleotide.

The invention provides for a drug substance obtained by the method for predicting nephrotoxicity of the present invention or by the method for screening a library of drug substances.

A pharmaceutical composition comprising the drug substance obtained by the method for predicting nephrotoxicity of the present invention or by the method for screening a library of drug substances and a pharmaceutically acceptable diluent, solvent, carrier, salt and/or adjuvant.

The nucleic acid molecule of obtained by the method for predicting nephrotoxicity of the present invention or by the method for screening a library of drug substances or the pharmaceutical composition comprising such a molecule for use in a medicine.

DEFINITIONS

Drug Substance

Figures 1, 2:
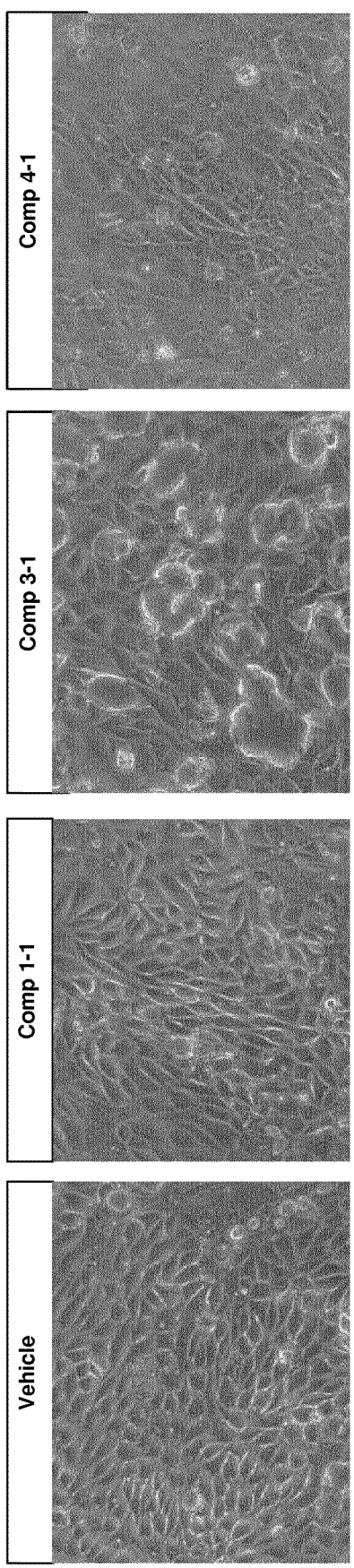
FIG. 1 shows morphological changes of PTEC-TERT1 cells treated with 100 µM oligonucleotide for 7 days.
FIG. 2 Schematically illustrates how the various biomarkers correlate with the toxicity observed in vivo. White indicates no toxicity (innocuous); light gray indicate mild toxicity; intermediate gray indicate medium toxicity; and dark gray indicate high toxicity.

The term "drug substance" in the context of the present application is generally to be understood as an active ingredient for the treatment, alleviation or prevention of a disease or condition. The drug substance can also be understood as a composition comprising the active ingredient, e.g. a pharmaceutical composition. Generally, any drug substance can be subject to the in vitro nephrotoxicity prediction method of the present invention. In some embodiments the drug substance is selected from the group consisting of nucleic acid based molecules, anti-cancer agents; aminoglycosides; antibacterial agents, anti-viral agents; anti-fungal agents, anti-inflammatory agents and immunosuppressant agents. Examples of antibacterial agents with known nephrotoxicity are polymyxins, such as colistin. In some embodiments the drug substance is a nucleic acid molecule selected from a RNAi agents, an antisense oligonucleotide or an aptamer. In some embodiments the drug substance is an antisense oligonucleotide.

A library of drug substances is to be understood as a collection of drug substances which have a recognizable chemical structure in common. Generally a library of drug substances is based on a parent or ancestral drug substance which it is desired to improve upon, for example in the context of the present application the parent drug substance has been found to elicit nephrotoxicity in vivo.

Immortalized Cell Line

The term "immortalized cell line" in the context of the present invention is to be understood as a population of cells descended from a single cell in a multicellular organism, where the cells have been modified to escape normal cellular senescence to allow continuous proliferation or division of the cells. Immortalized cells can be grown for prolonged periods in vitro. The mutations required for immortality can occur naturally or be intentionally induced e.g. using viral vectors, deletion of genes, induction of genes or induction of proteins such as telomerases or fusion with immortal cells such as cancer cells.

Primary Cell Culture

The term "primary cell culture" in the context of the present invention is to be understood as a population of cells isolated from a specific tissue in an animal. The primary cell culture is cultivated without prior genetic manipulations or clonal selection, it may however be purified using e.g. FACS or selective growth conditions. The primary cell culture can either be fresh or established from cryopreserved tissue.

Target Nucleic Acid

According to the present invention, the target nucleic acid can be a nucleic acid which encodes a mammalian protein and may for example be a gene, a RNA, a mRNA, and pre-mRNA, a mature mRNA or a cDNA sequence. The target nucleic acid can also be a microRNA, a long-non-coding RNA, a small nucleolar RNA or a transfer RNA.

Nucleic Acid Molecule

The term "nucleic acid molecule" or "therapeutic nucleic acid molecule" as used herein is defined as it is generally understood by the skilled person as a molecule comprising two or more covalently linked nucleosides. The nucleic acid molecule(s) referred to in the method of the invention are generally therapeutic oligonucleotides below 50 nucleotides in length. The nucleic acid molecules may be or comprise an antisense oligonucleotide, or may be another oligomeric nucleic acid molecule, such as a RNAi agent, an aptamer, or a ribozyme. Nucleic acid molecules are commonly made in the laboratory by solid-phase chemical synthesis followed by purification. When referring to a sequence of the nucleic acid molecule, reference is made to the sequence or order of nucleobase moieties, or modifications thereof, of the covalently linked nucleotides or nucleosides. The nucleic acid molecule of the invention is man-made, and is chemically synthesized, and is typically purified or isolated. The nucleic acid molecule of the invention may comprise one or more modified nucleosides or nucleotides.

In some embodiments, the nucleic acid molecule of the invention comprises or consists of 8 to 40 nucleotides in length, such as from 9 to 35, such as from 10 to 30, such as from 11 to 22, such as from 12 to 20, such as from 13 to 18 or 14 to 16 contiguous nucleotides in length.

In some embodiments, the nucleic acid molecule or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if a nucleic acid molecule is said to include from 10 to 30 nucleotides, both 10 and 30 nucleotides are included.

In some embodiments, the contiguous nucleotide sequence comprises or consists of 8, 9, 10, 11, 12, 13, 14, 15, 16, 17, 18, 19, 20, 21, 22, 23, 24, 25, 26, 27, 28, 29 or 30 contiguous nucleotides in length The nucleic acid molecule(s) are typically for modulating the expression of one or more target nucleic acids in a mammal. In some embodiments the nucleic acid molecules, such as for siRNAs and antisense oligonucleotides, are typically for inhibiting the expression of an RNA in a mammal, such as a mRNA or microRNA, for example. The nucleic acid molecules may therefore be effective at modulating the expression of one or more target nucleic acids in a mammal.

In one embodiment of the invention the nucleic acid molecule is selected from a RNAi agent, an antisense oligonucleotide or an aptamer.

In some embodiments the nucleic acid molecule is a phosphorothioate nucleic acid molecule.

In some embodiments the nucleic acid molecule comprises phosphorothioate internucleoside linkages.

In some embodiments the nucleic acid molecule(s) may be conjugated to non-nucleosidic moieties (conjugate moieties).

In some embodiments the nucleic acid molecules used or identified in the method of the invention comprise at least one stereodefined phosphorothioate internucleoside linkage.

A library of nucleic acid molecules is to be understood as a collection of variant nucleic acid molecules. The purpose of the library of nucleic acid molecules can vary. In some embodiments, the library of nucleic acid molecules is composed of oligonucleotides with different nucleobase sequences, for example it may be a library of nucleic acid molecules which are designed across a target nucleic acid (e.g. a RNA sequence), for example a library of antisense oligonucleotides or RNAi agents generated by a mRNA gene-walk with the purpose of identifying regions on the target nucleic acid where nucleic acid molecules efficiently modulate the target nucleic acid. In some embodiments, the library of nucleic acid molecules is composed of oligonucleotides with overlapping nucleobase sequence targeting a specific region on the target nucleic acid with the purpose of identifying the most potent sequence within the library of nucleic acid molecules. In some embodiments, the library of nucleic acid molecules is a library of nucleic acid molecule design variants (child nucleic acid molecules) of a parent or ancestral nucleic acid molecule, wherein the nucleic acid molecule design variants retaining the core nucleobase sequence of the parent nucleic acid molecule. In some embodiments the library of nucleic acid molecule variants (child nucleic acid molecules) differs from the parent nucleic acid molecule in one or more design parameters. The purpose of such a library is to improve the parent nucleic acid molecule, for example in the context of the present application the parent nucleic acid molecule has been found to elicit nephrotoxicity in vivo.

Antisense Oligonucleotides

The term "Antisense oligonucleotide" as used herein is defined as nucleic acid molecules capable of modulating expression of a target gene by hybridizing to a target nucleic acid, in particular to a contiguous sequence on a target nucleic acid. Antisense oligonucleotides generally contain one or more stretches of DNA or DNA-like nucleosides. The antisense oligonucleotides are not essentially double stranded and are therefore not siRNAs. Preferably, the antisense oligonucleotides of the present invention are single stranded.

In some embodiments, the antisense oligonucleotide(s) are capable of recruiting RNaseH, and may, for example be a gapmer oligonucleotide as defined herein, comprising one or more 2' sugar modified nucleosides in the flanks, such as 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides or mixtures of these (mixed wing gapmer), or may be a gap-breaker oligonucleotide.

In some embodiments, the antisense oligonucleotides are mixmers. Mixmer oligonucleotides typically comprise alternating regions of high affinity 2' sugar modified nucleosides, such as 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides, with short regions of 1-4 or 1-3 DNA nucleosides. Typically a mixmer will comprise alternating regions with short stretches of DNA, for example $[LNA]_{1-5}[DNA]_{1-3}[LNA]_{1-4}[DNA]_{1-3}[LNA]_{1-4}[DNA]_{1-3}$.

Various mixmer designs are highly effective, for example when targeting microRNA (antimiRs), microRNA binding sites on mRNAs (Blockmirs) or as splice switching oligomers (ASOs). See for example WO2007/112754 (LNA-AntimiRs™), WO2008/131807 (LNA splice switching oligos).

In some embodiments, the oligonucleotide may be a TINY LNA oligonucleotide of 7-10 nucleotides in length. Such TINY LNAs are disclosed in WO2009/043353, herein incorporated by reference. They are typically use to inhibit microRNAs and microRNA families, and may be full LNA modified (i.e. each nucleoside is a LNA nucleoside). It is also preferred that as with gapmer and mixmer oligonucleotides, the internucleoside linkages comprise phosphorothioate internucleoside linkages, and as with the oligonucleotides referred to herein may be fully phosphorothiolates oligonucleotides.

Antisense oligonucleotides are typically between 7-30 nucleotides in length, such as between 7-10 nucleotides (e.g. TINY LNAs) or 10-14 nucleotides (e.g. shortmers or short gapmers) or 12-20 or 10-22 or 10-24 nucleotides in length.

iRNA

As used herein, the terms "RNAi", "RNAi agent," "iRNA agent", "RNA interference agent" or "siRNA" as used interchangeably herein, refer to an oligonucleotide molecule that contains RNA nucleosides and which mediates the targeted cleavage of a target nucleic acid, such as an RNA transcript, via an RNA-induced silencing complex (RISC) pathway. iRNA directs the sequence-specific degradation of mRNA through a process known as RNA interference (RNAi). The iRNA modulates, e.g., inhibits, the expression of the target nucleic acid in a cell, e.g., a cell within a subject, such as a mammalian subject.

The RNAi agent subjected to the method of the invention can either be a double stranded RNA (dsRNA) or a single stranded RNA molecule that interacts with a target nucleic acid sequence, such as a target RNA sequence, via the RISC pathway to direct the cleavage of the target nucleic acid. Double stranded RNAi agents are generally between 20 and 50 nucleotides in length, such as between 25 and 35 nucleotides in length, and interacts with the endonuclease known as Dicer which is believed to processes dsRNA into 19.-23 base pair short interfering RNAs with characteristic two base 3' overhangs which are then incorporated into an RNA-induced silencing complex (RISC). Double stranded RNAi agents may siRNA molecules composed of a sense stand and and antisense strand forming a duplex together. Alternatively it can be an oligonucleotide that forms a secondary hairpin structure which essentially makes it double stranded in the region of the hairpin, such molecules are also termed shRNA's. Effective extended forms of Dicer substrates have been described in U.S. Pat. Nos. 8,349,809 and 8,513,207, hereby incorporated by reference. Upon binding to the appropriate target mRNA, one or more endonucleases within the RISC cleave the target to induce silencing. Single-stranded RNAi agents bind to the RISC endonuclease Argonaute 2, which then cleaves the target mRNA. Single-stranded iRNAs are generally 15-30 nucleotides long and are chemically modified, e.g. including modified internucleoside linkages and potentially also modified nucleosides. The design and testing of single-stranded siRNAs are described in U.S. Pat. No. 8,101,348 and in Lima et al., (2012) Cell I 50: 883-894, hereby incorporated by reference. dsRNA's may be chemically modified in the same manner as the single stranded RNAi agents.

Aptamer

As used herein, the term aptamer refers to an oligonucleotide or peptide that forms a three-dimensional structure capable of modulating a target through a ligand-target interaction, such as a ligand-protein interaction or a ligand-DNA helix interaction. Oligonucleotide aptamers can be formed of DNA, RNA or modified nucleosides or a mixture of these. Aptamers are effective via their three dimensional structure not through target hybridization as for antisense oligonucleotides or RNAi agents.

Modified Internucleoside Linkages

Modified internucleoside linkages may, for example, be selected from the group comprising phosphorothioate, diphosphorothioate and boranophosphate. In some embodiments, the modified internucleoside linkages are compatible with the RNaseH recruitment of the oligonucleotide to be tested in the method of the invention, for example phosphorothioate, diphosphorothioate or boranophosphate.

In some embodiments the internucleoside linkage comprises sulphur (S), such as a phosphorothioate internucleoside linkage. In some embodiments the oligonucleotides used or identified in the method of the invention comprise at least one stereodefined phosphorothioate internucleoside linkage.

A phosphorothioate internucleoside linkage is particularly useful due to nuclease resistance, beneficial pharmakokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly an internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(RH)—O—, O—PO(OCH$_3$)—O—, —O—PO(NRH)—O—, —O—PO(OCH$_2$CH$_2$S—R)—O—, —O—PO(BH$_3$)—O—, —O—PO(NHRH)—O—, —O—P(O)$_2$—NRH—, —NRH—P(O)$_2$—O—, —NRH—CO—O—, —NRH—CO—NRH—, and/or the internucleoside linker may be selected form the group consisting of: —O—CO—O—, —O—CO—NRH—, —NRH—CO—CH$_2$—, —O—CH$_2$—CO—NRH—, —O—CH$_2$—CH$_2$—NRH—, —CO—NRH—CH$_2$—, —CH$_2$—NRHCO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NRH—, —O—CH$_2$—CH$_2$—NRH—CO—, —CH$_2$—NCH$_3$—O—CH$_2$—, where RH is selected from hydrogen and C$_{1-4}$-alkyl.

Nuclease resistant linkages, such as phosphothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. In some embodiment, all the internucleoside linkages in the oligonucleotide are phosphorothioate linkages.

Stereodefined Internucleotide Linkages

In the context of the present invention the term "stereodfined" refers to nucleic acid molecules, such as oligonucleotides including antisense, RNI and aptamer molecules, where at least one phosphorothioate internucleoside linkage present in the oligonucleotide has defined stereochemistry, i.e. either Rp or Sp. In some embodiments all of the phosphorothioate internucleoside linkages in a stereodefined oligonucleotide may be stereodefined, i.e. each phosphorothioate internucleoside linkage is independently selected from the group consisting of Rp and Sp phosphorothioate internucleoside linkages.

Typically, oligonucleotide phosphorothioates are synthesized as a random mixture of Rp and Sp phosphorothioate linkages (also referred to as a racemic mixture). In the present invention, gapmer phosphorothioate oligonucleotides are provided where at least one of the phosphorothioate linkages of the gap region oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Such oligonucleotides may be referred as being stereodefined, stereoselective or stereospecified: They comprise at least one phosphorothioate linkage which is stereospecific. The terms stereodefined and stereospecified/stereoselective may be used interchangeably herein. The terms stereodefined, stereoselective and stereospecified may be used to describe a phosphorothioate internucleoside linkage (Rp or Sp), or may be used to described a oligonucleotide which comprises such a phosphorothioate internucleoside linkage. It is recognized that a stereodefined oligonucleotide may comprise a small amount of the alternative stereoisomer at any one position, for example Wan et al reports a 98% stereoselectivity for the gapmers reported in NAR, November 2014.

Modulation of Expression

The term "modulation of expression" as used herein is to be understood as an overall term for an oligonucleotide's ability to alter the amount of a nucleic acid target when compared to the amount of the nucleic acid target before administration of the oligonucleotide. Alternatively modulation of expression may be determined by reference to a control experiment. It is generally understood that the control is an individual or target cell treated with a saline composition or an individual or target cell treated with a non-targeting oligonucleotide (mock). It may however also be an individual treated with the standard of care.

One type of modulation is an oligonucleotide's ability to inhibit, down-regulate, reduce, suppress, remove, stop, block, prevent, lessen, lower, avoid or terminate expression of the nucleic acid target e.g. by degradation of mRNA or blockage of transcription. Another type of modulation is an oligonucleotide's ability to restore, increase or enhance expression of nucleic acid target e.g. by repair of splice sites or prevention of splicing or removal or blockage of inhibitory mechanisms such as microRNA repression.

In some embodiments of the invention, when the target of the oligonucleotide of the invention is present in the EGFR expressing cells, the method of the invention may further comprise the step of determining the level of target modulation (e.g. inhibit for siRNAs or antisense oligonucleotides) in the population of EGFR expressing cells after treatment with the oligonucleotides (e.g. this may occur in parallel or as part of the measurement of the at least one biomarker step). In this regard the method of the invention may be used to determine the comparative potency or effectiveness of the oligonucleotide and the comparative toxicity, allowing for the selection of potent non-toxic compounds for use in vivo. It will be understood that the determination of compound potency/effectiveness may be performed in a separate in vitro experiment, either in the EGFR expressing cells, particularly cells which are expressing the target.

Modified Oligonucleotides

Non-modified DNA and RNA molecules are rapidly degraded in vivo, and as such are of little use therapeutically. Typically, the oligonucleotide(s) used in the method of the invention are therefore modified. One widely used modification is the use of phosphorothioate internucleoside linkages, which is known to stabilize oligonucleotides from nucleolytic degradation, as well as providing desirable pharmacological properties. In some embodiments the oligonucleotide(s) comprise phosphorothioate internucleoside linkages.

Another desirable modification are those which confer higher affinity of the oligonucleotide to the target nucleic acid, so called high affinity modified nucleotides, which include bicyclic "LNA" nucleosides as well as numerous 2' substituted nucleosides.

High Affinity Modified Nucleosides

In some embodiments, the oligonucleotide comprises one or more high affinity modified nucleoside. A high affinity modified nucleoside is a modified nucleoside which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example 2' sugar modified nucleosides, such as many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligonucleotide(s) may comprise one or more nucleosides which have a modified sugar moiety, i.e. a modification of the sugar moiety when compared to the ribose sugar moiety found in naturally occurring DNA and RNA nucleosides.

Numerous nucleosides with modification of the ribose sugar moiety have been made, primarily with the aim of improving certain properties of oligonucleotides, such as affinity and/or nuclease resistance. Such modifications include those where the ribose ring structure is modified, e.g. by replacement with a hexose ring (HNA).

Sugar modifications also include modifications made via altering the substituent groups on the ribose ring to groups other than hydrogen, or the 2'—OH group naturally found in DNA and RNA nucleosides. Substituents may, for example be introduced at the 2', 3', 4' or 5' positions of the ribose ring. Nucleosides with modified sugar moieties also include 2' modified nucleosides, such as 2' substituted nucleosides. Numerous 2' substituted nucleosides have been found to have beneficial properties when incorporated into oligonucleotides, such as enhanced nucleoside resistance and enhanced affinity. In one embodiment the nucleic acid molecule(s) or library of such molecules comprises one or more 2' sugar modified nucleoside.

In addition to the 2' substitution there are other modifications including a modification at position 2 of the ribose ring, such as introduction of a bicyclic ring, which typically have a biradicle bridge between the C2 and C4 carbons on the ribose ring (also known as locked nucleic acid or LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

2' Sugar Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

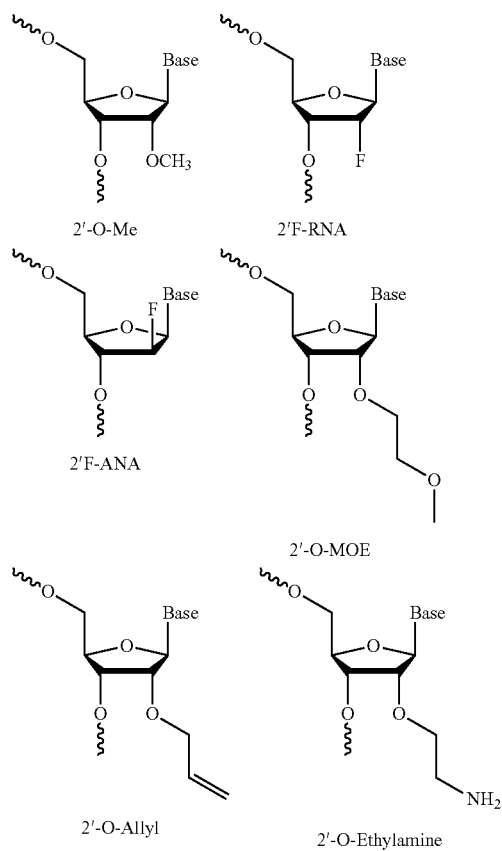

Locked Nucleic Acid Nucleosides (LNA).

In some embodiments oligonucleotides are LNA oligonucleotides, i.e. they comprise at least one LNA nucleoside.

LNA monomers (also referred to as bicyclic nucleic acids, BNA) are nucleosides where there is a biradical between the 2' and 4' position of the ribose ring. The 2'-4' biradical is also referred to as a bridge. LNA monomers, when incorporated into a oligonucleotides are known to enhance the binding affinity of the oligonucleotide to a complementary DNA or RNA sequence, typically measured or calculated as an increase in the temperature required to melt the oligonucleotide/target duplex ($T_m$).

The LNA oligomer may be a single stranded antisense oligonucleotide.

The LNA used in the oligonucleotide compounds of the invention may have the structure of the general formula I

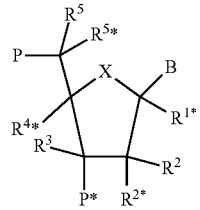

Formula 1 wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a bivalent linker group consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of $C(R^aR^b)$—$C(R^aR^b)$—, $C(R^aR^b)$—O—, $C(R^aR^b)$—$NR^a$—, $C(R^aR^b)$—S—, and $C(R^aR^b)$—C$(R^aR^b)$—O—, wherein each $R^a$ and $R^b$ may optionally be independently selected. In some embodiments, $R^a$ and $R^b$ may be, optionally independently selected from the group consisting of hydrogen and $_{C1-6}$alkyl, such as methyl, such as hydrogen.

In some embodiments, $R^{4*}$ and $R^{2*}$ together designate the biradical —O—$CH(CH_2OCH_3)$-(2'O-methoxyethyl bicyclic nucleic acid—Seth at al., 2010, J. Org. Chem)—in either the R- or S-configuration.

In some embodiments, $R^{4*}$ and $R^{2*}$ together designate the biradical —O—$CH(CH_2CH_3)$-(2'O-ethyl bicyclic nucleic acid—Seth at al., 2010, J. Org. Chem).—in either the R- or S-configuration.

In some embodiments, $R^{4*}$ and $R^{2*}$ together designate the biradical —O—$CH(CH_3)$—.—in either the R- or S-configuration. In some embodiments, $R^{4*}$ and $R^{2*}$ together designate the biradical —O—$CH_2$—O—$CH_2$— (Seth at al., 2010, J. Org. Chem).

In some embodiments, $R^{4*}$ and $R^{2*}$ together designate the biradical —O—NR—$CH_3$— (Seth at al., 2010, J. Org. Chem).

In some embodiments, the LNA units have a structure selected from the following group:

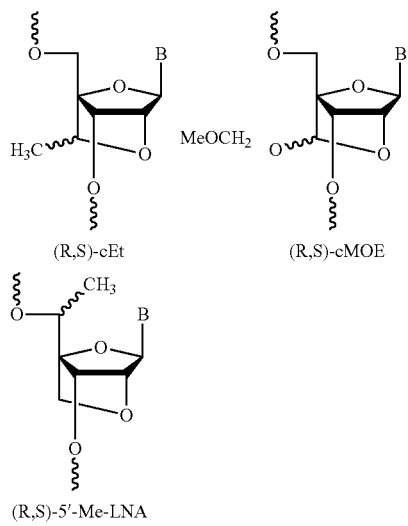

(R,S)-cEt    (R,S)-cMOE (R,S)-5'-Me-LNA

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —$CH_3$, —$CH_2$—$CH_3$, —$CH_2$—O—$CH_3$, and —CH=$CH_2$. Suitably in some embodiments, either $R^5$ or $R^{5*}$ are hydrogen, where as the other group ($R^5$ or $R^{5*}$ respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, ON, O—C(=O)$NJ_1J_2$, N(H)C(=NH)$NJ_1J_2$ or N(H)C(=X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl or a protecting group. In some embodiments either $R^5$ or $R^{5*}$ is substituted $C_{1-6}$ alkyl. In some embodiments either $R^5$ or $R^{5*}$ is substituted methylene wherein preferred substituent groups include one or more groups independently selected from F, $NJ_1J_2$, $N_3$, ON, $OJ_1$, $SJ_1$, O—C(=O)$NJ_1J_2$, N(H)C(=NH)NJ, $J_2$ or N(H)C(O)N(H)$J_2$. In some embodiments each $J_1$ and $J_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —$C(R^aR^b)$—O—, —$C(R^aR^b)$—C$(R^cR^d)$—O—, —$C(R^aR^b)$—$C(R^cR^d)$—$C(R^eR^f)$—O—, —$C(R^aR^b)$—O—$C(R^cR^d)$—, —$C(R^aR^b)$—O—$C(R^cR^d)$—O—, —$C(R^aR^b)$—$C(R^cR^d)$—, —$C(R^aR^b)$—$C(R^cR^d)$—C$(R^eR^f)$—, —$C(R^a)$=$C(R^b)$—$C(R^cR^d)$—, —$C(R^aR^b)$—N$(R^c)$—, —$C(R^aR^b)$—$C(R^cR^d)$— N$(R^e)$—, —$C(R^aR^b)$—N$(R^c)$—O—, and —$C(R^aR^b)$—S—, —$C(R^aR^b)$—$C(R^cR^d)$—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH=CH— For all chiral centers, asymmetric groups may be found in either R or S orientation.

In some embodiments, $R^{4*}$ and $R^{2*}$ together designate the biradical C($R^a R^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^a R^b$)—O—C($R^c R^d$)—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some embodiments, $R^{1*}$, $R^2$, $R^3$. are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein $R^c$ is $C_{1-12}$ alkyloxy. In some embodiments $R^{4*}$ and $R^{2*}$ together designate a biradical —$Cq_3q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)N $J_1J_2$ or N(H)C(=X=N(H)$J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^5$. are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) C($R^a R^b$)—O—, wherein $R^a$ and $R^b$ are each independently halogen, $C_1$-$C_{12}$ alkyl, substituted $C_1$-$C_{12}$ alkyl, $C_2$-$C_2$ alkenyl, substituted $C_2$-$C_2$ alkenyl, $C_2$-$C_2$ alkynyl, substituted $C_2$-$C_{12}$ alkynyl, $C_1$-$C_{12}$ alkoxy, substituted $C_1$-$C_{12}$ alkoxy, $OJ_1SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C(q3)(q4); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$ and; each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group. Such compounds are disclosed in WO2009006478A, hereby incorporated in its entirety by reference.

In some embodiments, $R^{4*}$ and $R^{2*}$ form the biradical—Q-, wherein Q is C($q_1$)($q_2$)C($q_3$)($q_4$), C($q_1$)=C($q_3$), C[=C($q_1$)($q_2$)]-O($q_3$)($q_4$) or C($q_1$)($q_2$)-O[=O($q_3$)($q_4$)]$_1$; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, ON, C(=O)$OJ_1$, C(=O)—NJ$_1$J$_2$, C(=O) J$_1$, —C(=O)NJ$_1$J$_2$, N(H)C(=NH)NJ$_1$J$_2$, N(H)C(=O)NJ$_1$J$_2$ or N(H)C(=S)NJ$_1$J$_2$; each J$_1$ and J$_2$ is, independently, H, C$_{1-6}$ alkyl, C$_{2-6}$ alkenyl, C$_{2-6}$ alkynyl, C$_{1-6}$ aminoalkyl or a protecting group; and, optionally wherein when Q is C(q$_1$)(q$_2$)(q$_3$)(q$_4$) and one of q$_3$ or q$_4$ is CH$_3$ then at least one of the other of q$_3$ or q$_4$ or one of q$_1$ and q$_2$ is other than H. In some embodiments, R$^{1*}$, R$^2$, R$^3$, R$^5$, R$^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, R$^{1*}$, R$^2$, R$^3$, R$^5$, R$^{5*}$ are independently selected from the group consisting of hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl or substituted C$_{2-6}$ alkynyl, C$_{1-6}$ alkoxyl, substituted C$_{1-6}$ alkoxyl, acyl, substituted acyl, C$_{1-6}$ aminoalkyl or substituted C$_{1-6}$ aminoalkyl. In some embodiments, R$^{1*}$, R$^2$, R$^3$, R$^5$, R$^{5*}$ are hydrogen. In some embodiments, R$^{1*}$, R$^2$, R$^3$ are hydrogen and one or both of R$^5$, R$^{5*}$ may be other than hydrogen as referred to above and in WO 2007/134181 or WO2009/067647 (alpha-L-bicyclic nucleic acids analogs).

Further bicyclic nucleoside analogues and their use in antisense oligonucleotides are disclosed in WO2011 115818, WO2011/085102, WO2011/017521, WO09100320, WO10036698, WO09124295 & WO09006478. Such nucleoside analogues may in some aspects be useful in the compounds of present invention.

In some embodiments the LNA used in the oligonucleotide compounds of the invention preferably has the structure of the general formula II:

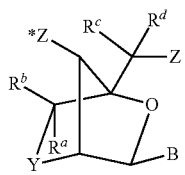

Formula II wherein Y is selected from the group consisting of —O—, —CH$_2$O—, —S—, —NH—, N(R$^e$) and/or —CH$_2$—; Z and Z* are independently selected among an internucleotide linkage, R$^H$, a terminal group or a protecting group; B constitutes a natural or non-natural nucleotide base moiety (nucleobase), and R$^H$ is selected from hydrogen and C$_{1-4}$-alkyl; R$^a$, R$^b$ R$^c$, R$^d$ and R$^e$ are, optionally independently, selected from the group consisting of hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH$_2$); and R$^H$ is selected from hydrogen and C$_{1-4}$-alkyl. In some embodiments R$^a$, R$^b$ R$^c$, R$^d$ and R$^e$ are, optionally independently, selected from the group consisting of hydrogen and C$_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

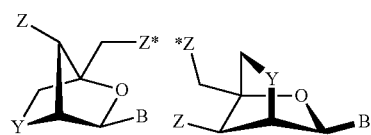

Specific exemplary LNA units are shown below:

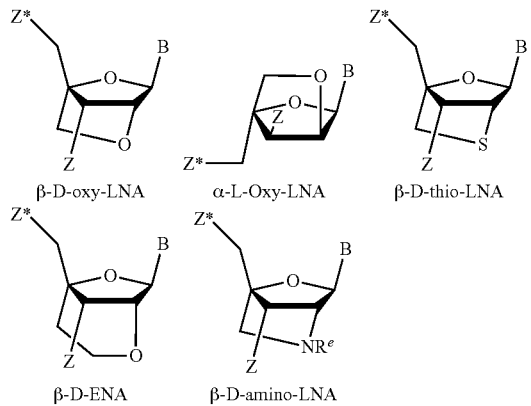

β-D-oxy-LNA    α-L-Oxy-LNA    β-D-thio-LNA

β-D-ENA    β-D-amino-LNA

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). R$^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Certain examples of LNA nucleosides are presented in Scheme 1.

Scheme 1

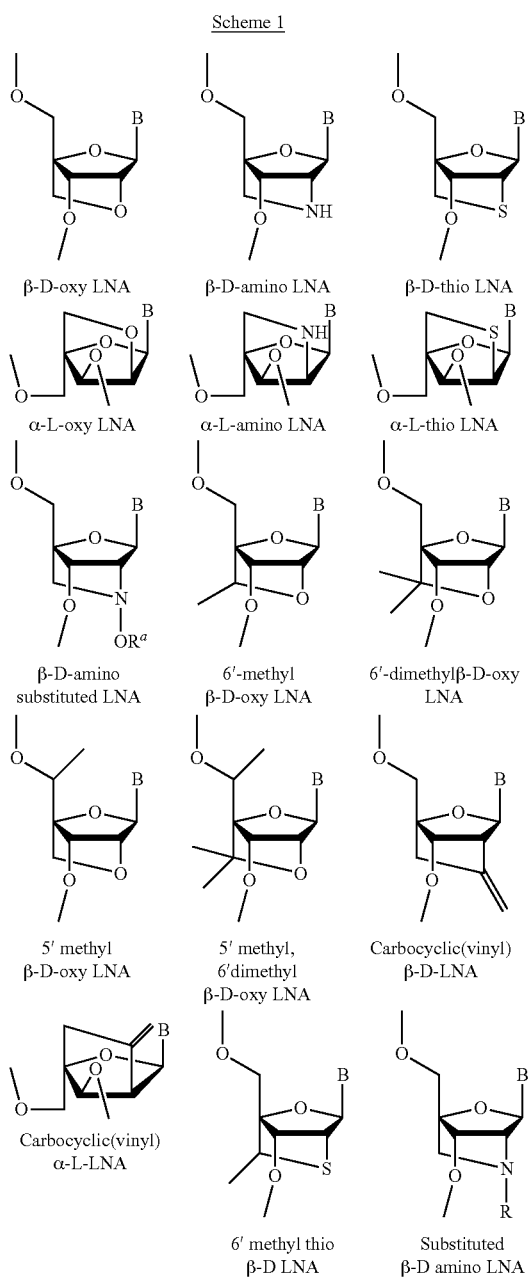

As illustrated in the examples, in some embodiments of the invention the LNA nucleosides in the oligonucleotides are beta-D-oxy-LNA nucleosides.

Gapmer

The term "gapmer" as used herein refers to an antisense oligonucleotide which comprises a region of RNase H recruiting oligonucleotides (gap) which is flanked 5' and 3' by regions which comprise one or more affinity enhancing modified nucleosides (flanks or wings). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flank comprises affinity enhancing modified nucleosides) and for tailmers the 5' flank is missing (i.e. the 3' flank comprises affinity enhancing modified nucleosides).

Gapmer Designs

Gapmer oligonucleotides are widely used to inhibit a target RNA in a cell, such as a mRNA or viral RNA, via an antisense mechanism (and may therefore also be called antisense gapmer oligonucleotides). In a gapmer structure the oligonucleotide comprises at least three distinct structural regions a 5'-flank, a gap and a 3'-flank, F-G-F' in '5->3' orientation. The G region or gap region comprises a region of at least 5 contiguous nucleotides which are capable or recruiting RNaseH, such as a region of DNA nucleotides, e.g. 6-14 DNA nucleotides or other nucleosides which are capable of recruiting RNase H, e.g., alpha-L-oxy-LNA, 2'-Flouro-ANA and UNA. The gap region is flanked 5' and 3' by regions (F and F' also termed flanking regions or wing regions) which comprise one or more affinity enhancing modified nucleosides, such as 2' modified nucleotides. In some embodiments, the flanking regions may be 1-8 nucleotides in length.

In further embodiments region F (5' flank or 5' wing) is attached to the '5 end of region G and region F' (3' flank or 3' wing) is attached to the '3 end of region G. Region F and F', comprises contains or consists independently of at least one modified nucleoside such as at least 2, at least 3, at least 4, at least 5, at least 6, at least 7 modified nucleosides. In an embodiment region F and/or F' comprises or consists independently of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides. The F region is defined by having at least on modified nucleoside at the 5' end and at the 3' end of the region. The F' region is defined by having at least on modified nucleoside at the 5' end and at the 3' end of the region.

In some embodiments, the modified nucleosides in region F and/or F' have a 3' endo structure.

In an embodiment, one or more of the modified nucleosides in region F and/or F' are 2' modified nucleosides. In one embodiment all the nucleosides in Region F and/or F' are 2' modified nucleosides.

In another embodiment region F and/or F' comprises DNA and/or RNA in addition to the 2' modified nucleosides. Flanks comprising DNA and/or RNA are characterized by having a 2' modified nucleoside in the 5' end and the 3'end of the F and/or F' region. In one embodiment the region F and/or F' comprises DNA nucleosides, such as from 1 to 3 contiguous DNA nucleosides, such as 1 to 3 or 1 to 2 contiguous DNA nucleosides. The DNA nucleosides in the flanks should preferably not be able to recruit RNase H. In some embodiments the 2' modified nucleosides and DNA and/or RNA nucleosides in the F and/or F' region alternate with 1 to 3 2' modified nucleosides and 1 to 3 DNA and/or RNA nucleosides. Such flanks can also be termed alternating flanks. The length of region F and/or F' in oligonucleotides with alternating flanks may independently be 4 to 10 nucleosides, such as 4 to 8, such as 4 to 6 nucleosides, such as 4, 5, 6 or 7 modified nucleosides. In some embodiments only the F region of the oligonucleotide is alternating. In some embodiments only the F' region of the oligonucleotide is alternating.

Specific examples of region F and/or F' with alternating nucleosides are $2'_{1-3}$-$N'_{1-4}$-$2'_{1-3}$ $2'_{1-2}$-$N'_{1-2}$-$2'_{1-2}$-$N'_{1-2}$-$2'_{1-2}$ Where 2' indicates a modified nucleoside and N' is a RNA or DNA. In some embodiments all the modified nucleosides in the alternating flanks are LNA and the N' is DNA. In a further embodiment one or more of the 2' modified nucleosides in region F and/or F' are independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F and/or F' region comprises both LNA and a 2' substituted modified nucleoside. These are often termed mixed wing or mixed flank oligonucleotides.

In one embodiment of the invention all the modified nucleosides in region F and/or F' are LNA nucleosides. In a further embodiment all the nucleosides in Region F and/or F' are LNA nucleosides. In a further embodiment the LNA nucleosides in region F and/or F' are independently selected from the group consisting of oxy-LNA, thio-LNA, amino-LNA, cET, and/or ENA, in either the beta-D or alpha-L configurations or combinations thereof. In a preferred embodiment region F and/or F' comprise at least 1 beta-D-oxy LNA unit, at the 5' end of the contiguous sequence.

In further embodiments, Region G (gap region) preferably comprise, contain or consist of at least 4, such as at least 5, such as at least 6, at least 7, at least 8, at least 9, at least 10, at least 11, at least 12, at least 13, at least 14, at least 15 or at least 16 consecutive nucleosides capable of recruiting the aforementioned nuclease, in particular RNaseH. In a further embodiment region G comprise, contain or consist of from 5 to 12, or from 6 to 10 or from 7 to 9, such as 8 consecutive nucleotide units capable of recruiting aforementioned nuclease.

The nucleoside units in region G, which are capable of recruiting nuclease are in an embodiment selected from the group consisting of DNA, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue.

In a still further embodiment at least one nucleoside unit in region G is a DNA nucleoside unit, such as from 1 to 12 DNA units, such as 2, 3, 4, 5, 6, 7, 8, 9, 10 or 11 DNA units, preferably from 2 to 12 DNA units, such as from 4 to 12 DNA units, more preferably from 5 to 11, or from 2 to 10, 4 to 10 or 6 to 10 DNA units, such as from 7 to 10 DNA units, most preferably 8, 9 or 10 DNA units. In some embodiments, region G consists of 100% DNA units.

In further embodiments the region G may consist of a mixture of DNA and other nucleosides capable of mediating RNase H cleavage. Region G may consist of at least 50% DNA, more preferably 60%, 70% or 80% DNA, and even more preferred 90% or 95% DNA.

In a still further embodiment at least one nucleoside unit in region G is an alpha-L-LNA nucleoside unit, such as at least one alpha-L-LNA, such as 2, 3, 4, 5, 6, 7, 8 or 9 alpha-L-LNA. In a further embodiment, region G comprises the least one alpha-L-LNA is alpha-L-oxy-LNA. In a further embodiment region G comprises a combination of DNA and alpha-L-LNA nucleoside units.

In some embodiments the size of the contiguous sequence in region G may be longer, such as 12, 13, 14, 15, 16, 17, 18, 19 or 20 nucleoside units.

In some embodiments, nucleosides in region G have a 2' endo structure.

In the gapmer designs reported herein the gap region (Y') may comprise one or more stereodefined phosphorothaiote linkage, and the remaining internucleoside linkages of the gap region may e.g. be non-stereodefined internucleoside linkages, or may also be stereodefined phosphorothioate linkages.

LNA Gapmer

The term LNA gapmer is a gapmer oligonucleotide wherein at least one of the affinity enhancing modified nucleosides is an LNA nucleoside. In some embodiments both flanks of the gapmer oligonucleotide comprise at least one LNA unit, and in some embodiments, all of the nucleoside of the flanks are LNA nucleosides.

In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. Typically the LNA load of the flanks of LNA gapmers is lower than that for 2'substituted nucleosides, and examples of LNA gapmer designs include $[LNA]_{1-4}$-$[DNA]_{5-15}$-$[LNA]_{1-4}$.

In some embodiments, the gapmer is a so-called shortmer as described in WO2008/113832 incorporated herein by reference.

Further gapmer designs are disclosed in WO2004/046160, WO2007/146511 and incorporated by reference.

Mixed Wing Gapmer

The term mixed wing gapmer or mixed flank gapmer refers to a LNA gapmer wherein at least one of the flank regions comprise at least one LNA nucleoside and at least one non-LNA modified nucleoside, such as at least one DNA nucleoside or at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises only LNA nucleosides (e.g. 5' or 3') and the other flank (3' or 5' respectfully) comprises 2' substituted modified nucleoside(s) and optionally LNA nucleosides.

Gapbreaker

The term "gapbreaker oligonucleotide" is used in relation to a gapmer capable of maintaining RNAseH recruitment even though the gap region is disrupted by a non-RNaseH recruiting nucleoside (a gap-breaker nucleoside, E) such that the gap region comprise less than 5 consecutive DNA nucleosides. Non-RNaseH recruiting nucleosides are for example nucleosides in the 3' endo conformation, such as LNA's where the bridge between C2' and C4' of the ribose sugar ring of a nucleoside is in the beta conformation, such as beta-D-oxy LNA or ScET nucleoside. The ability of gapbreaker oligonucleotide to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA.

In some embodiments, the oligonucleotide of the invention is a gapbreaker oligonucleotide. In some embodiments the gapbreaker oligonucleotide comprise a 5'-flank (F), a gap (G) and a 3'-flank (F'), wherein the gap is disrupted by a non-RNaseH recruiting nucleoside (a gap-breaker nucleoside, E) such that the gap contain at least 3 or 4 consecutive DNA nucleosides. The gap-breaker design is based upon the gapmer designs, e.g. those disclosed here (e.g. Region F corresponds to the X' region of the gapmer above, and region F' corresponds to the region Z' of the gapmer described herein), with the exception that the gap region (region Y') comprises a gap-breaker nucleoside. In some embodiments the gapbreaker nucleoside (E) is an LNA nucleoside where the bridge between C2' and C4' of the ribose sugar ring of a nucleoside is in the beta conformation and is placed within the gap region such that the gap-breaker LNA nucleoside is flanked 5' and 3' by at least 3 (5') and 3 (3') or at least 3 (5') and 4 (3') or at least 4(5') and 3(3') DNA nucleosides, and wherein the oligonucleotide is capable of recruiting RNaseH.

The gapbreaker oligonucleotide can be represented by the following formulae:

F-G-E-G-F'; in particular $F_{1-7}$-$G_{3-4}$-$E_1$-$G_{3-4}$-$F'_{1-7}$

D'-F-G-F', in particular $D'_{1-3}$-$F_{1-7}$-$G_{3-4}$-$E_1$-$G_{3-4}$-$F'_{1-7}$ F-G-F'-D'', in particular $F_{1-7}$-$G_{3-4}$-$E_1$-$G_{3-4}$-$F'_{1-7}$-$D''_{1-3}$ D'-F-G-F'-D'', in particular $D'_{1-3}$-$F_{1-7}$-$G_{3-4}$-$E_1$-$G_{3-4}$-$F'_{1-7}$-$D''_{1-3}$ Where G represents DNA nucleosides and region D' and D'' are optional and may additional 5' and/or 3' nucleosides, such as DNA nucleosides.

In some embodiments the gapbreaker nucleoside (E) is a LNA, beta-D-oxy LNA or ScET or another LNA nucleoside, such as beta-D-nucleoside disclosed herein.

Stereodefined Gapmers

In some embodiments, the child oligonucleotides originating from a parent gapmer oligonucleotide has at least one of the internucleoside linkages of the gap region which is stereodefined, and optionally wherein the gap region comprises both Rp and Sp internucleoside linkages.

In some embodiments, in the child oligonucleotide(s) (and optionally the parent), at least one of the internucleoside linkages of the gap region are stereodefined, and wherein the central region comprises both Rp and Sp internucleoside linkages.

In some embodiments, in the child oligonucleotide(s) (and optionally the parent), the internucleoside linkages within region G are all stereodefined phosphorothioate internucleoside linkages. In some embodiments, in the child oligonucleotide(s) (and optionally the parent), the internucleoside linkages within region F and F' are stereodefined phosphorothioate internucleoside linkages. In some embodiments in the child oligonucleotide(s) (and optionally the parent), the internucleoside linkages between region F and G and between region G and F' are stereodefined phosphorothioate internucleoside linkages. In some embodiments in the child oligonucleotide(s) (and optionally the parent), all the internucleoside linkages within the contiguous nucleosides of regions F-G-F' are stereodefined phosphorothioate internucleoside linkages.

The introduction of at least one stereodefined phosphorothioate linkages in the gap region of an oligonucleotide may be used to modulate the biological profile of the oligonucleotide, for example it may modulate the toxicity profile. In some embodiments, 2, 3, 4 or 5 of the phosphorothioate linkages in the gap region in the child oligonucleotide(s) (and optionally the parent), are stereodefined. In some embodiments the remaining internucleoside linkages in the gap region are not stereodefined: They exist as a racemic mixture of Rp and Sp in the population of oligonucleotide species. In some embodiments in the child oligonucleotide(s) (and optionally the parent), the remaining internucleoside linkage in the oligonucleotide are not stereodefined. In some embodiments in the child oligonucleotide(s) (and optionally the parent), all the internucleoside linkages in the gap region are stereodefined.

In some embodiments 1, 2, 3, 4, 5, 6, 7, 8, 9, 10, 11, 12, 13, or 14 of the linkages in the gap region of the oligomer are stereoselective phosphorothioate linkages.

In some embodiments 5%, 10%, 15%, 20%, 25%, 30%, 35%, 40%, 45%, 50%, 55%, 60%, 65%, 70%, 75%, 80%, 85%, 90%, or 95% of the linkages in the oligomer (e.g. gapmer) are stereoselective phosphorothioate linkages. In some embodiments all of the phosphorothioate linkages in the oligomer are stereoselective phosphorothioate linkages. In some embodiments the all the internucleoside linkages of the oligomer are stereodefined phosphorothioate linkages.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference).

Efficacy and Therapeutic Index

The drug substances identified by the method of the invention may in addition the toxicity be tested as part of the method of the invention to determine that they are still effective drug substances. In particular with nucleic acid based drug substances it has been observed that when toxicity is reduced this is in part due to a reduction in the efficacy of the drug substance. In one aspect of the invention the decrease in the toxicity grade does not result in a significant decrease in the efficacy. In some embodiments the therapeutic index (TI) of the drug substance selected according to the method of the invention is improved when compared to a toxic reference substance. For the purpose of the present invention TI refers to the dose of the drug substance that causes adverse effects in the kidney in 50% of subjects (TD50) divided by the dose that leads to the desired efficacy (target knockdown or pharmacological effect) in 50% of subjects (EC50). In some embodiments the TI is increased by at least 10%, such as at least 15, 25, 50, 75, 100, 150, 200, 250 or 300% when compared to a toxic reference drug substance, such as Compound 4-1 herein or a toxic parent oligonucleotide or toxic parent drug substance. For experimental purposes, assuming the target is present in mice, TD50 and EC50 may be determined in mice in a seven day mouse study. If for example for nucleic acid molecules, the sequence conservation in mice is unfavorable, other model species may be used, e.g. rat, monkey, dog, pig or monkey (e.g. cynomolgus monkey). In some embodiments the increase in TI is due to an increased TD50 and a low or no decrease in EC50. The increase in TI may also be the result of improvements on both parameters. In relation to the method of the invention the increase in TI is not brought about by only improving the efficacy of the drug substance (i.e. reduced EC50).

The method of the invention may therefore comprise an additional step of screening the library of (e.g. child) drug substances for their efficacy in modulating, e.g. inhibiting, their target.

Alternatively, the method of the invention may comprise an additional step of testing the selected drug substances (e.g. stereodefined oligonucleotide variants) with a reduced toxicity to determine their efficacy as drug substances, e.g. as antisense oligonucleotides. For antisense oligonucleotides the efficacy may be determined by the oligonucleotides ability to recruit RNaseH, or in some embodiments may be the ability to modulate the expression of the target in a cell, in vitro, or in some embodiments, in vivo.

Conjugate Moieties

In some embodiments, the conjugate moiety comprises or is a carbohydrate, non nucleosidic sugars, carbohydrate complexes. In some embodiments, the carbohydrate is selected from the group consisting of galactose, lactose, n-acetylgalactosamine, mannose, and mannose-6-phosphate.

In some embodiments, the conjugate moiety comprises or is selected from the group of protein, glycoproteins, polypeptides, peptides, antibodies, enzymes, and antibody fragments, In some embodiments, the conjugate moiety is a lipophilic moiety such as a moiety selected from the group consisting of lipids, phospholipids, fatty acids, and sterols.

In some embodiments, the conjugate moiety is selected from the group consisting of small molecules drugs, toxins, reporter molecules, and receptor ligands.

In some embodiments, the conjugate moiety is a polymer, such as polyethyleneglycol (PEG), polypropylene glycol.

In some embodiments the conjugate moiety is or comprises a asialoglycoprotein receptor targeting moiety, which may include, for example galactose, galactosamine, N-formyl-galactosamine, Nacetylgalactosamine, N-propionyl-galactosamine, N-n-butanoyl-galactosamine, and N-isobutanoylgalactos-amine. In some embodiments the conjugate moiety comprises a galactose cluster, such as N-acetylgalactosamine trimer. In some embodiments, the conjugate moiety comprises a GalNAc (N-acetylgalactosamine), such as a mono-valent, di-valent, tri-valent of tetra-valent GalNAc. Trivalent GalNAc conjugates may be used to target the compound to the liver (see e.g. U.S. Pat. No. 5,994,517 and Hangeland et al., Bioconjug Chem. 1995 November-December; 6(6):695-701, WO2009/126933, WO2012/089352, WO2012/083046, WO2014/118267, WO2014/179620, & WO2014/179445), see specific examples in FIG. 2. These GalNAc references and the specific conjugates used therein are hereby incorporated by reference.

DETAILED DESCRIPTION OF THE INVENTION

Prediction of In Vivo Toxicity

The methods described herein may be used to predict the in vivo toxicity of a drug substance in a mammal. Toxicity of any compound is typically dependent upon its dose, and as such the methods of the invention may be used to assess a compounds comparative toxicity profile as compared to a negative control, and/or a drug substance whose toxicity profile is known, or compared to a population (or a library) of drug substances, such as a library of nucleic acid molecules. In this respect, the prediction of in vivo toxicity may be an assessment of the comparative risk of encountering a toxicity phenotype, such as nephrotoxicity, when the drug substance(s) are administered in vivo in a mammal.

When assessing the safety of a drug substance one of the parameters that is investigated is the impact of the substance on the kidney, e.g. accumulation in renal proximal tubules, tubular degenerative/regenerative changes (tubulotoxicity), biomarkers for acute kidney injury, like KIM-1, which are detectable in the urine. Kidney related toxicities are generally known as nephrotoxicity.

The methods of the invention may be used to predict the in vivo toxicity (e.g. nephrotoxicity), or alternatively stated to determine the likely in vivo toxicity profile (e.g. nephrotoxicity), of a drug substance in vivo in a mammal. In one embodiment of the invention the in vivo nephrotoxicity is acute kidney injury and/or tubular degradation. The methods of the invention may be used to identify drug substances which are not toxic (e.g. not nephrotoxic) in vivo, when used at dosages which are effective in modulating their target, or at therapeutically effective doses. The methods of the present invention therefore allows the selection of drug substances which do not exhibit dose limiting toxicity (e.g. nephrotoxicity) when used in vivo at effective dosages. It will be recognized that it is an advantage to have a wide safety margin when selecting drug substances for in vivo or for therapeutic use, and as such the methods of the invention may be used to identify or select drug substances which do not elicit in vivo toxicity, such as nephrotoxicity, when dosed effectively, or at higher doses, e.g. at up to 2× the effective dose, or up to 3× the effective dose, or up to 5× the effective dose, or up to 10× the effective dose. The methods of the invention may therefore be used to identify drug substances for in vivo use which have a maximum tolerated dose higher (e.g. at least 2×, at least 3×, at least 5×, at least 10×) than the effective dose. In this regard the methods of the invention may be used to select drug substances which have a suitable therapeutic index (TI) for safe therapeutic administration, or an improved therapeutic index as defined herein.

The present invention establishes EGF as a reliable biomarker in an in vitro cell based assay for prediction of in vivo nephrotoxicity of a drug substance.

One aspect of the present invention is an in vitro method for predicting in vivo nephrotoxicity of a drug substance in a mammal, said method comprising the steps of:
  a) culturing cells expressing epidermal growth factor receptor (EGFR) in a suitable cell culture media containing at least 4 ng/ml of epidermal growth factor (EGF);
  b) administering the drug substance to said cell culture;
  c) incubating the cells for a period of time; and
  d) subsequently measuring the EGF level in the supernatant;
wherein an increase in EGF in the supernatant is indicative of a drug substance which is, or is predicted to be, associated with nephrotoxicity.

The increase in extracellular EGF levels can be evaluated in relation to a reference value obtained from non-treated cells, cells treated with vehicle (vehicle control, i.e the solvent in which the drug substance is dissolved, e.g. saline, DMSO or other suitable solvents) or cells treated with non-toxic reference drug substance where the non-toxic drug substance has been validated as non-toxic in vivo (an in vivo validated non-toxic drug substance). Such a non-toxic drug substance can for example be the antisense oligonucleotide compound 1-1 with SEQ ID NO: 1, in particular if the drug substance(s) that is being subjected to the assay of the invention is a nucleic acid molecule(s), such as an antisense oligonucleotide(s).

In some embodiments, the alteration in the EGF biomarker is determined as the percentage of the reference value. As is illustrated in the examples, the present inventors have found that an increase in the level of EGF in the supernatant (extracellular EGF) above 175%, such as at least 200%, such as at least 250%, such as at least 300%, such as at least 350%, such as at least 400% relative to the reference value is predicative of nephrotoxicity of the drug compound. In embodiments where the drug substance is an antisense oligonucleotide the oligonucleotide is administered to the cells in a concentration above 10 micro molar, such as between 20 and 150 micro molar, such as between 30 and 120 micro molar, such as between 50 and 100 micro molar.

In further embodiments the EGF level in the supernatant is further compared to a second reference value obtained from cells treated with a nephrotoxic drug substance, where the nephrotoxic reference drug substance has been validated to cause nephrotoxicity in vivo (an in vivo validated nephrotoxic reference drug substance). In some embodiments, the method of the invention may therefore further comprise the method steps of the invention using the administration of one or more drug substances with a known toxicity (e.g. nephrotoxicity) profile, such as a positive control drug substance which is known to elicit nephrotoxicity and/or a negative control drug substance which is known not to elicit nephrotoxicity, and a comparison of the level of EGF in the supernatant from the administration of the drug substance(s) with the levels obtained from the positive and/or negative controls. The generation of data from of a negative control (vehicle control or in vivo validated non-toxic drug substance) and a positive control (in vivo validated nephrotoxic drug substance) allows determination of an assay window that can be used to normalize for batch to batch variation in the assay. The assay window (AW) is the difference between the non-toxic reference drug substance or vehicle control and the nephrotoxic reference drug substance. In order to compare different drug substances, e.g. from a library of drug substances it is an advantage to determine the toxicity grade of each drug substance. This is done according to the following formula $$\left( \frac{[EGF] \text{ drug substance} - [EGF] \text{ non-toxic reference} + (AW/100))}{[EGF] \text{ toxic reference} - [EGF] \text{ non-toxic reference} + (AW/100))} \right) \times 100\%$$

The toxicity grade can be used to differentiate the level of nephrotoxicity, or predicted level of nephrotoxicity of a drug substance.

In some embodiments the toxicity grade can be used to differentiate the predicted in vivo nephrotoxicity as follows:

| Predicted in vivo toxicity | Toxicity grade |
| --- | --- |
| High | 50-100 |
| Medium | 20-50 |
| Low | 6-20 |
| Innocuous | 0-5 |

In particular a drug substance is predicted as nephrotoxic when the toxicity grade is above 6, such as above 20, such as above 50.

In one embodiment the toxicity grade is assessed using the conditions for oligonucleotide treatment described in the "materials and methods" section where the oligonucleotide is administered to the cells in a concentration above 10 micro molar, such as between 20 and 150 micro molar, such as between 30 and 120 micro molar, such as between 50 and 100 micro molar.

In some embodiment the in vivo validated nephrotoxic reference drug substance is antisense oligonucleotide compound 4-1 with SEQ ID NO: 4.

In addition or alternatively, the control data may be determined by comparing a library of drug substances, in particular a library of nucleic acid molecules such as antisense oligonucleotides, RNAi agents or aptamers, using the method of the invention, either in series or in parallel, and comparing the level of EGF biomarker after administration of each member of the library of drug substances. Such a method allows for the selection of comparatively less toxic (such as nephrotoxic) drug substances. In some embodiments, the control data may be or may include control data which is from a cell culture sample which has not been administered a drug substance or vehicle control (day 0 control). Such a sample may be obtained immediately prior to the administration step.

Complementary Biomarkers

As is illustrated in the examples, the present inventors have found that intracellular adenosine triphosphate (ATP) levels and extracellular kidney injury molecule-1 (KIM-1) protein levels or intracellular KIM-1 mRNA levels can serve as complementary biomarkers to the EGF biomarker further strengthening the predictability of the method of the invention.

In an embodiment of the invention the method for predicting in vivo nephrotoxicity of a drug substance in a mammal, said method comprising the steps of:
a) culturing cells expressing epidermal growth factor receptor (EGFR) in a suitable cell culture media containing at least 4 ng/ml of epidermal growth factor (EGF);
b) administering the drug substance to said cell culture;
c) incubating the cells for a period of time; and
d) subsequently measuring the EGF level in the supernatant and the intracellular ATP levels;
wherein an increase in the EGF level in the supernatant and a decrease in the intracellular ATP level is indicative of a drug substance which is, or is predicted to be, associated with nephrotoxicity.

A decrease of cellular ATP in relation to the reference value (negative control) to at least 80%, such at least about 70%, such as at least about 60%, such as at least 50%, such as at least 40% relative to the reference value is indicative of an enhanced propensity to trigger nephrotoxicity in vivo. The ATP biomarker is compared to a set of controls as already described in relation to the EGF biomarker. In particular to a negative control reference value obtained from non-treated cells, cells treated with vehicle (vehicle control, i.e the solvent in which the drug substance is dissolved, e.g. saline, DMSO or other suitable solvents) or cells treated with non-toxic reference drug substance where the non-toxic drug substance has been validated as non-toxic in vivo (an in vivo validated non-toxic drug substance). Such a non-toxic drug substance can for example be compound 1-1 with SEQ ID NO: 1, in particular if the drug substance(s) that is being subjected to the assay of the invention is a nucleic acid molecule(s), such as an antisense oligonucleotide(s). The intracellular ATP biomarker may further be compared to a second reference value obtained from cells treated with a nephrotoxic drug substance, where the nephrotoxic reference drug substance has been validated to cause nephrotoxicity in vivo (an in vivo validated nephrotoxic reference drug substance).

In some examples the EGF biomarker alone was not sufficient to predict the nephrotoxicity of a compound with known in vivo nephrotoxicity. In these instances KIM-1 as an in vitro biomarker showed to complement the EGF biomarker very well. As illustrated in FIG. 2 the combination of EGF and KIM-1 biomarkers in the assay of the invention resulted in a 100% prediction of compounds with known in vivo nephrotoxicity.

In an embodiment of the invention the method for predicting in vivo nephrotoxicity of a drug substance in a mammal, said method comprising the steps of:
a) culturing cells expressing epidermal growth factor receptor (EGFR) in a suitable cell culture media containing at least 4 ng/ml of epidermal growth factor (EGF);
b) administering the drug substance to said cell culture;
c) incubating the cells for a period of time; and
d) subsequently measuring the EGF level and the KIM-1 protein levels in the supernatant;
wherein an increase in the EGF or KIM-1 level in the supernatant is indicative of a drug substance which is, or is predicted to be, associated with nephrotoxicity.

As an alternative or as supplement to the extracellular KIM-1 protein levels the intracellular level of KIM-1 mRNA level may also be measured.

In some embodiments, the alteration in the extracellular KIM-1 biomarker is determined as the percentage of the control reference value (negative control). As is illustrated in the examples, the present inventors have found that an increase in the level of KIM-1 in the supernatant (extracellular KIM-1) above 175%, such as at least 200%, such as at least 250%, such as at least 300%, such as at least 350%, such as at least 400% relative to the reference value is predicative of nephrotoxicity of the drug compound, In particular when the drug substance is a nucleic acid molecule, such as an antisense oligonucleotide, an increase in KIM-1 levels is predictive, even if there for the same compound is no observable increase in EGF levels and/or decrease in ATP levels. Without being bound by theory we suspect that the mechanism that elicits the KIM-1 biomarker increase in vitro is different from the mechanism that elicits the increase in extracellular EGF levels or the decrease in intracellular ATP levels.

It should be recognized that the actual level of increase/decrease of the biomarker will depend on many factors including the properties of the cell culture, the density of the cell culture, the concentration of drug substance used, and the incubation time of the drug substances. Relevant parameters are described in the following sections.

Cell Cultures

In the examples of the present invention several cell cultures have been tested. Both primary cell cultures as well as immortalized cell cultures appear to function in the method of the invention as long as they express functional epidermal growth factor receptor (EGFR). The EGFR is endogenous meaning that it is expressed by the cell.

The method of the invention may be used to determine the likely toxicity in vivo of the drug substance(s) in model species such as rodent species such as mouse, rat or rabbit, or pig (e.g. minipig) or dog, or primates, such as monkeys (e.g. cynomolgus monkey), or may be used to determine the likely toxicity in vivo of the drug substance(s) in humans. The inventors have found that the use of primary EGFR expressing epithelial cells or primary hepatocytes or immortalized EGFR expressing epithelial cell are predictive of the toxicity profile seen in vivo on rodent studies as well as in human clinical trials. In particular epithelia cells originating from kidney or lung tissue which express functional EGFR are suitable in the method of the invention. In one embodiment the epithelial cell does not originate from the eye, in particular not from the retinal pigment epithelia, in particular the cell culture is not an ARPE19 cell culture.

In one embodiment of the invention the cells expressing functional EGFR consume EGF present in the growth medium when cultured under normal conditions (without being subjected to drug or vehicle substances). The rate of EGF consumption is preferably at least 50% EGF from the medium over 72 hours, when the cells are grown under regular conditions without being subjected to drug or vehicle substances. Some cell cultures may have a higher rate of EGF consumption such as at least 50% of the EGF in the medium over 60 hours, such as at least 50% of the EGF in the medium over 48 hours. In order to measure the EGF consumption in a cell culture it is important that the medium comprises EGF. The EGF consumption of a cell culture can be asses according to the principles of Example 8.

The level of EGF needed in the medium both to assess the EGF consumption of the untreated cell culture as well as measuring the increase in EGF levels following drug substance treatment can vary with the cell type. In some embodiments the EGF in the cell culture medium comprises between 3 and 20 ng EGF/ml culture medium, such as between 5 and 15 ng/ml, such as between 6 and 10 ng/ml, such as at least 3 ng/ml, such as at least 4 ng/ml, such as at least 5 ng/ml, such as at least 6 ng/ml, such as at least 7 ng/ml, such as at least 8 ng/ml, such as at least 9 ng/ml. In a preferred embodiment the cell culture medium comprises between 8 and 15 ng/ml. In a further preferred embodiment the cell culture medium comprises at least 10 ng EGF/ml culture medium.

In one embodiment cells which express functional EGFR can be selected from the group consisting of epithelial cell, endothelial cell, mesenchymal cells, neuroectodermal cells and hepatocytes. In particular cell cultures originating from epithelial cells or hepatocytes are used in the method of the present invention.

In one embodiment the epithelial cells can be in the form of a mammalian primary cell culture, such as a cell culture selected from the group consisting of rodent primary epithelial cells, such as mouse or rat primary epithelial cells; pig (e.g. minipig) epithelial cells, dog epithelia cells and non-human primate primary epithelial cells, such as monkey (e.g. cynomolgus monkey) or human primary epithelial cells. In a preferred embodiment the cell culture is obtained from a rat or a human primary epithelial cells or hepatocytes. In addition to being obtainable from various species the cell culture may also be obtained from various organs, such as epithelial cells from the gastrointestinal tract, lungs, reproductive and urinary tracts, kidney, exocrine and endocrine glands. In one embodiment the epithelial cell culture is a kidney epithelial cell culture or a lung epithelial cell culture. Since the present invention sets out to predict nephrotoxicity kidney epithelial cells from selected from the group consisting of proximal tubule epithelial cells, distal tubule epithelial cells and collecting duct epithelial cells are particularly relevant. Specific examples of primary cell cultures are those made from human PTEC or rat PTEC cells. In addition to epithelial cell cultures the examples of the present invention also show that other cell types expressing EGFR can be used, for example primary hepatocytes.

In another embodiment the cells expressing EGFR are cultured from an immortalized cell line. Specific examples of cell cultures obtained from immortalized cell lines are human PTEC-TERT-1, ciPTEC, HK-2, NKi-2 or human A549 cell lines. An example of an immortalized cell line which does express EGFR, but does not have EGF consumption is CACO2 cells. In one embodiment of the invention the EGFR expressing cell line is not a CACO2 cell line or an ARPE19 cell line.

Administering the Drug Substance

The drug substance to be assessed in the method of the present invention can be administered to the cell culture by common methods known in the art, such as passive diffusion, electroporation, sonication, cell squeezing, hydrostatic pressure, nanoparticles (e.g. liposomes), magnetofection and cell penetrating peptides. Nucleic acid molecules are generally administered using transfection or through the process known as gymnosis (also known as naked delivery, see Stein et al., NAR 2010 38(1) e3 or Soifer et al., Methods Mol Biol 2012, 815: 333-46), although other administration options also can be applied. In the examples it can be seen that the prediction of the in vitro nephrotoxicity using the EGF biomarker is independent on whether the antisense oligonucleotide is administered to the cell culture by transfection or by gymnosis. The mode of administration needs to be adapted to the properties of the cell culture. Some cell types are more prone to take oligonucleotides up by gymnosis, as demonstrated for PTEC type cell lines, whereas other cell lines are more suitable for transfection as seen for the A549 cell line. The mode of administration is therefore subject to optimization such that the best mode of administration is investigated for a particular cell culture.

In one embodiment of the invention the nucleic acid molecule is administered by gymnosis, in particular if the nucleic acid molecule is single stranded oligonucleotides such as antisense oligonucleotides or singled stranded RNAi agents. Since its discovery over 5 years ago, gymontic delivery has become a standard tool used in oligonucleotide research, and is a well-established term used in the art. Typically, gymnotic delivery of oligonucleotides utilizes a concentration of oligonucleotide of between about 1 µM and about 1000 µM, such as between about 5 µM and about 1001 µM, such as between about 101 µM and about 50 µM, such as between about 20 µM and 40 µM such as about 25-35 µM. Suitably oligonucleotides may be administered to the cell culture, e.g. in PBS, to achieve a final concentration of 1-100 µM, such as 5-50 µM, such as 10 or 30 µM. One of the advantages of gymnotic delivery is that it resembles the delivery that occur in vivo, in that no additional chemicals are needed to get the oligonucleotides into the cell.

In another embodiment of the invention the nucleic acid molecule is administered by transfection, this approach is suitable both for single stranded and double stranded oligonucleotides. Transfection can be performed using standard methods known in the art, such as lipofection, cationic polymers, calcium phosphate etc. Typically, transfection utilize oligonucleotide concentration of between 0.5 ng and 50 ng, such as between 1 ng and 25 ng, such as between 2 ng and 15 ng, such as between about 3 ng and 10 ng. Suitably oligonucleotides may be administered to the cell culture, e.g. in PBS, to achieve a final concentration corresponding to those indicated above.

Incubation Time

The time between administration of the drug substance and the measurement of the relevant biomarkers is the incubation time or culturing time. For an in vitro toxicity assay to be as effective as possible the readout needs to be reproducible and consistently predict compounds with potential toxicity issues. Another relevant parameter is the time it takes to conduct the assay, the quicker it can be done the higher the throughput can be, which is highly relevant if the method of the invention is used to screen large libraries of drug substances. The incubation time is subject to optimization depending on cell culture and method of administration. In one embodiment of the invention the incubation time with the drug substance is between 1 and 9 days such as between 2 and 8 days, 3 and 7 days, or between 4 and 6 days, in particular between 2 and 6 days or between 3 and 6 days, such as 2, 3, 4, 5, 6, 7, 8 or 9 days. The inventors have found that for the extra cellular biomarkers, EGF and Kim-1, a sufficient reproducibility can be achieved using a 2 to 6 day incubation time, in particular biomarker measurements at day 3 and day 6 after administration show good results. In one embodiment of the invention a single stranded oligonucleotide is administered to the cell culture using gymnosis in a concentration of 50 to 100 µM and incubated for 3 to 6 days and EGF and/or KIM-1 is measured at these times.

In the case where the intracellular biomarker, ATP, is measured the incubation time the incubation time with the drug substance is between 5 and 10 days, such as between 6 and 9, in, such as 6, 7, 8 or 9 days.

In embodiments where the administration is performed using transfection the incubation time with the nucleic acid molecule is between 1 and 4 days, such as between 2 and 3 days, such as 1, 2, 3 or 4 days. In one embodiment of the invention a nucleic acid molecule is administered to the cell culture using transfection in a concentration of 1 to 20 ng and incubated for 1 to 3 days and EGF and/or KIM-1 is measured at these times.

Cell culture of mammalian cells is typically performed at or about 37° C., and may further comprise exogenous $CO_2$, such kept in an atmosphere of or about 5% $CO_2$. Cells in culture generally needs fresh medium on a regular basis such as every 2 to 4 days. If the incubation time exceeds 3 to 4 days the medium can be exchanged every 3 to 4 days. The fresh medium preferably contains a concentration of drug substance corresponding to the concentration given a day 0, to secure a continues presence of the drug substance during the incubation time.

One of the advantages of the present invention is the early read out of predictive toxicity biomarkers, relatively shortly after the initiation of the incubation period, and that the biomarkers used provide a reliable signal.

Screening Library of Variants to Identify Child Drug Substances with a Predicted Reduced Toxicity Profile In Vivo:

The invention provides for a method for selecting one or more drug substances suitable for in vivo administration to a mammal, from a library of drug substances, said method comprising the steps of:
 a) Obtaining a library of drug substances
 b) Administer each member of the library of drug substances to a cell culture expressing epidermal growth factor receptor (EGFR) and where the medium contains at least 4 ng/ml of epidermal growth factor (EGF);
 c) and culturing the cells in vitro for a period of time;
 d) measuring the amount of at least one nephrotoxicity biomarker; and e) selecting one or more drug substances wherein the toxicity grade is below 6.

In one embodiment of the invention the therapeutic index of the drug substance selected in step e) is decreased when compared to a toxic reference substance or parent drug substance.

The selected drug substance(s) may optionally administering in vivo to the mammal to confirm that the compound does not elicit nephrotoxicity. In particular rats are highly sensitive to nephrotoxic nucleic acid molecules, and therefore a relevant species for confirming the prediction obtained using the method of the present invention. Naturally other mammalian species mentioned herein may also be relevant.

In some embodiments, the library of drug substances is a library of nucleic acid molecules constituted of RNAi agents, an antisense oligonucleotides or aptamers.

In one embodiment the library of nucleic acid molecules have different nucleobase sequences, for example they may be a library of nucleic acid molecules which are designed across a target sequence (e.g. a mRNA), for example a library of antisense oligonucleotides or RNAi agents generated by a mRNA gene-walk.

In one embodiment the members of the library of nucleic acid molecules have identical nucleobase sequences in a contiguous stretch of the sequence, where the contiguous stretch is shorter than the nucleic acid molecule, with at least a subset of the molecules in the library. Such a "hot-spot" library may for example be a library of nucleic acid molecules which are designed across a target sequence of e.g. 50 to 100 nucleobases in length (e.g. a hot spot on a target RNA), where the members of the library is will be overlapping along this sequence with at least 4 to 14 nucleobases, such as 5 to 12 nucleobases such as 6 to 10 nucleobases. The library may for example be a library of antisense oligonucleotides or RNAi agents identifying the oligonucleotide with the highest TI targeting the identified hot-spot.

In some embodiments, the library of drug substances is a library of nucleic acid molecule variants (child nucleic acid molecules) of a parent nucleic acid molecule, wherein the parent nucleic acid molecule is toxic, such as nephrotoxic, and wherein step d) identifies one or more nucleic acid molecule variants which are less toxic than the parent nucleic acid molecule; wherein the oligonucleotide variants retaining the core nucleobase sequence of the parent nucleic acid molecule, such as an antisense oligonucleotide In some embodiments, the child nucleic acid molecules may be the same length as the parent nucleic acid molecule and retain the same nucleobase sequence. However, it is envisaged that, in some embodiments, the child nucleic acid molecules may be truncated, such as by the removal of a 5' and/or 3' terminal nucleotide, or may in some embodiments, have an additional nucleotide at the 5' and/or 3' end. Removal of one or more terminal high affinity nucleosides, such as a LNA nucleoside allows for the affinity of the nucleic acid molecule to the RNA target to be maintained, as the insertion of one or more LNA nucleosides into the gap region will increase the affinity to the RNA target. It is envisaged that, in some embodiments, the library of child nucleic acid molecules may comprise variants which have different flank regions, some being truncated, some having additional nucleosides, some having a sequence shifted one or two nucleosides (as measured to the RNA target), some with additional high affinity nucleosides in the flanks, so the library is a complex library of stereodefined phosphorothioate oligonucleotides with heterogeneous phosphorothioate internucleoside linkages, thereby allowing for the concurrent selection of child nucleic acid molecules which have a decreased toxicity as compared to the parent nucleic acid molecule.

The parent and child nucleic acid molecules share a common core nucleobase sequence. The common core nucleobase sequence (or contiguous nucleobase sequence) is typically at least 10 nucleobases long, such as at least 11, at least 12, at least 13, at least 14, at least 15, or at least 16 nucleobases long, and in some embodiments may be the same nucleobase sequence of the parent nucleic acid molecule. In some embodiments the parent and (at least a proportion of) the child nucleic acid molecules have the same nucleobase sequence across the length of the nucleic acid molecules. It is however envisaged that a proportion of the child nucleic acid molecules may, in some embodiments, comprise additional 5' or 3' nucleotides, such as an additional 1, 2 or 3 5' or 3' nucleotides. In addition or alternatively in some embodiments, a proportion of the child nucleic acid molecules may be truncated with regards the parent, e.g. may comprise 1, 2 or 3 nt truncation at the 5' or 3' end. In some embodiments, additional nucleobase or truncations of the nucleobase sequence of the (proportion of) child nucleic acid molecule (s) is a single nucleobase addition or truncation. In some embodiments, the child oligonucleotides, or a proportion thereof, may be shifted by a single nucleobase, or by 2 or 3 nucleobases in comparison to the parent nucleic acid molecule when aligned to the target sequence (in effect a truncation at one end, and an addition at the other). Additional nucleotides retain complementarity with the target nucleic acid sequence.

In some embodiments the library of nucleic acid molecule variants (child nucleic acid molecules) differs from the parent nucleic acid molecule in one or more design parameters. The design parameter can be selected from the group consisting of i) presence of one or more stereodefined phosphorothioate internucleoside linkages; ii) change in gap size; iii) introduction of a gap breaker; iv) change of wing size; v) introduction of 2' sugar modified nucleosides; and vi) change in the 2' sugar modified nucleoside composition in the wings introducing at least two different 2' modified nucleosides in the wings, such as LNA nucleosides and 2' substituted nucleosides, in particular LNA and MOE.

In some embodiments, the nucleic acid molecule variants are oligonucleotide variants. In some embodiments the oligonucleotide variants are antisense oligonucleotides.

In some embodiments the antisense oligonucleotide, is a gapmer oligonucleotide.

In some embodiments, the oligonucleotide variants are RNAi agents.

In some embodiments, the oligonucleotide variants differ from the parent oligonucleotide by the presence of one or more stereodefined phosphorothioate internucleoside linkages.

In some embodiments, the oligonucleotide variants are LNA oligonucleotides.

In some embodiments, the library of child antisense oligonucleotides are or comprise a population of child oligonucleotides with different gapmer designs, optionally including different mixed wing gapmer designs, gap-breaker designs, gap length and flank length.

The method of the invention may be used to identify stereodefined nucleic acid molecules with reduced in vivo toxicity (such as nephrotoxicity), in particular stereodefined antisense oligonucleotides.

The invention therefore provides for a particular method of reducing the toxicity of an antisense oligonucleotide (parent oligonucleotide) using stereodefined phosphorothioate internucleoside linkage, comprising the steps of
   a) Creating a library of stereodefined oligonucleotide variants (child oligonucleotides), retaining the core nucleobase sequence of the parent oligonucleotide;
   b) Screening the library created in step a) in a cell culture expressing epidermal growth factor receptor (EGFR) and where the medium contains at least 4 ng/ml of epidermal growth factor (EGF) (as per the method of the invention as described herein); and
   c) Identifying one or more stereodefined variants present in the library which has a reduced toxicity in the cell culture as compared to the parent oligonucleotide.

Optionally the method is repeated (reiterative screening), for example so that the one or more stereodefined variants identified by the method is used as a parent oligonucleotide in the next round of the screening method.

In the method of the invention, each member of the library created in step b) comprises at least one stereodefined phosphorothioate internucleoside linkage which differs from parent.

The methods of the invention may further comprise an additional subsequent step of manufacturing the one or more selected nucleic acid molecule variants which have a reduced toxicity using one of the methods of the invention. In some embodiments, the subsequent manufacture is in a scale of more than 1 g, such as more than 10 g. In some embodiments, the synthesis of the oligonucleotides for in vivo or in vitro screening steps is performed at a scale of less than 1 g, such as less than 0.5 g, such as less than 0.1 g.

In some embodiments, the methods further comprise the step of determining the in vitro or in vivo potency of either the library of drug substances, or of the one or more selected drug substances in the library identified in step c) or e).

The invention provides a method for predicting the (e.g. likely) in vivo nephrotoxicity of an oligonucleotide, such as a LNA oligonucleotide, said method comprising the steps of administering the oligonucleotide to a cell culture expressing epidermal growth factor receptor (EGFR) and where the medium contains at least 4 ng/ml of epidermal growth factor (EGF), incubating the cells in the presence of the oligonucleotide, e.g. for a period of between 2-9 days, such as 2-6 days, such as 3 days, and subsequently measuring at least one biomarker of toxicity, such as those described herein, e.g. by measuring the amount of EGF and/or KIM-1 released into the culture media, and optionally determining intracellular ATP levels. Suitably a reduction in cellular ATP levels is indicative of a nephrotoxic oligonucleotide, and elevation of EGF or KIM-1 in the culture media is indicative of a nephrotoxic oligonucleotide.

The invention provides for the use of an in vitro assay to determine the (e.g. likely) neperotoxicity of a drug substance, such as a nucleic acid molecule, such as an antisense oligonucleotide, such as an LNA oligonucleotide.

It will be recognized that, in some embodiments, the methods for predicting (or determining) the in vivo toxicity (e.g. nephrotoxicity), may be used to identify stereodefined variants of a parent oligonucleotide, where the sterodefined variants have reduced in vitro or in vivo toxicity.

Complementary Toxicity Assays

In addition to the method for predicting in vivo nephrotoxicity of a drug substance described in this application, the method may further be combined with methods for predicting other toxicities relevant to the development of a drug substance, in particular a therapeutic oligonucleotide, such as an antisense oligonucleotide.

In some embodiments, the method for predicting nephrotoxicity disclosed or claimed in the present application may be combined with a method for predicting immunotoxicity of drug substance, in particular an oligonucleotide.

One method for predicting immunotoxicity of a drug substance in particular of an oligonucleotide, comprises measuring at least one complement biomarker and/or at least one (such as at least two) cytokine biomarkers in blood samples subjected to the drug substance. In a particular embodiment immunotoxicity is predicted by measuring at least one complement biomarker and at least two cytokine biomarkers in blood samples subjected to the drug substance, in particular an oligonucleotide.

In some embodiments the method of the invention further includes or provides a method of predicting immunotoxicity comprising the steps of a) administering the drug substance, in particular an oligonucleotide, to human blood (isolated from the body); b) incubating the samples between 30 min to 8 hours; c) stop the reaction; and d) measure at least two, three, four, five of or all of the following biomarkers: i) complement biomarkers C3a and C5a, and/or ii) cytokine biomarkers interleukin 6 (IL6), interleukin 8 (IL8), tumor necrosis factor alpha (TNFa), and monocyte chemoattractant protein-1 (MCP1); wherein a mean increase above about 2 fold compared to a control in at least two of the biomarkers is indicative of in vivo immunotoxicity of the drug substance, such as the oligonucleotide. The blood sample of step a) is typically obtained from at least one healthy human subject, such as at least two or at least three healthy human subjects. Generally, the blood samples are not mixed. In some embodiments at least one of the complement biomarkers C3a and C5a is measured in combination with at least two cytokine biomarkers selected from the group consisting of interleukin 6 (IL6), interleukin 8 (IL8), tumor necrosis factor alpha (TNFa), and monocyte chemoattractant protein-1 (MCP1). In some embodiments at least cytokine biomarkers interleukin 8 (IL8), and monocyte chemoattractant protein-1 (MCP1) are measured.

In some embodiments blood samples from at least 3 donors are used. Typically the blood is obtained from healthy donors (i.e. isolated from the body). In some embodiments the measurements from the 3 different blood samples are averaged to achieve an immunotoxicity read out.

In some embodiments, the method disclosed or claimed in the present application may be combined with a method for predicting hepatotoxicity of a drug substance, in particular an oligonucleotide. A method for predicting in vivo hepatotoxicity of an oligonucleotide is described in WO2017/067970, hereby incorporated by reference. In brief one method of predicting in vivo hepatotoxicity of an oligonucleotide comprises the steps of a) administering the oligonucleotide to a population of primary mammalian hepatocyte cells (or population of hepatocytes derived from induced pluripotent stem cells) in vitro in a cell culture media; b) culturing the cells in vitro in the cell culture media for a period of time, such as between 1 and 14 days, in particular between 2 and 7 days; and c) subsequently measuring the level of lactate dehydrogenase (LDH) released into the culture media, and/or measuring the level of cellular ATP levels; wherein an increase in lactate dehydrogenase in the cell culture media, such as a 20% increase compared to a control, or a decrease in cellular ATP levels, such as a 20% decrease compared to a control, is indicative of an oligonucleotide which is, or is predicted to be hepatotoxic in vivo in a mammal. Further biomarkers that can supplement the hepatotoxicity prediction are microRNA-122 released into the culture media, where an increase in microRNA-122 in the cell culture medium is predictive of hepatotoxicity, and intracellular glutathione (GSH) levels, where a reduction in GHS levels is predictive of hepatotoxicity.

In some embodiments of the invention the method for predicting in vivo nephrotoxicity is combined with a method of predicting in vivo immunotoxicity and a method of predicting in vivo hepatotoxicity, such as the methods described above.

Pharmaceutical Composition

In a further aspect, the invention provides a drug substance or salts thereof obtained by the method of the invention. In a further aspect the drug substance or salts thereof obtained by the method of the invention may be formulated into a pharmaceutical composition comprising any of the aforementioned drug substance and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 μM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Drug substances obtained by the method of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The invention provides methods for treating or preventing a disease, comprising administering a therapeutically or prophylactically effective amount of a drug substance or salts thereof obtained by the method of the invention or a pharmaceutical composition of the invention to a subject suffering from or susceptible to the disease.

The invention also relates to a drug substance or salts thereof obtained by the method of the invention or a pharmaceutical composition as defined herein for use as a medicament.

The drug substance or salts thereof obtained by the method of the invention or a pharmaceutical composition according to the invention is typically administered in an effective amount.

The invention also provides for the use of the drug substance or salts thereof obtained by the method of the invention for the manufacture of a medicament for the treatment of a disorder as referred to herein, or for a method of the treatment of as a disorder as referred to herein.

Embodiments of the Invention

The following embodiments of the present invention may be used in combination with any other embodiments described herein.

1. An in vitro method for predicting in vivo nephrotoxicity of a drug substance in a mammal, said method comprising the steps of:
 a. culturing cells expressing epidermal growth factor receptor (EGFR) in a suitable cell culture media containing at least 4 ng/ml of epidermal growth factor (EGF);
 b. administering the drug substance to said cell culture;
 c. incubating the cells for a period of time; and
 d. subsequently measuring the EGF level in the supernatant;
wherein an increase in EGF in the supernatant is indicative of a drug substance which is, or is predicted to be, associated with nephrotoxicity.

2. The method according to embodiment 1, wherein EGF level in the supernatant is compared to a reference value obtained from cells treated with vehicle control or a non-toxic reference drug substance, where the non-toxic drug substance has been validated as non-toxic in vivo.

3. The method according to embodiment 2, wherein the non-toxic reference drug substance is an oligonucleotide compound consisting of CGTcagtatgcgAATc (SEQ ID NO: 1), wherein lower case letters represent DNA units, bold upper case letters represent beta-D-oxy-LNA units, all LNA C are 5'methyl C and all internucleoside linkages are phosphorothioate linkage.

4. The method according to embodiment 3, wherein a level of EGF in the supernatant above 200% relative to the vehicle control or non-toxic reference value is predicative of nephrotoxicity of the drug substance.

5. The method according to embodiment 2 to 4, wherein EGF level in the supernatant is further compared to a second reference value obtained from cells treated with a nephrotoxic drug substance, where the nephrotoxic reference drug substance has been validated to cause nephrotoxicity in vivo.

6. The method according to embodiment 5, wherein an assay window (AW) is determined as the difference between the non-toxic reference drug substance or vehicle control and the nephrotoxic reference drug substance.

7. The method according to embodiment 5, wherein the toxic reference drug substance is an oligonucleotide compound consisting of GCtgtgtgagcttGG (SEQ ID NO: 4), wherein lower case letters represent DNA units, bold upper case letters represent beta-D-oxy-LNA units, all LNA C are 5'methyl C and all internucleoside linkages are phosphorothioate linkage.

8. The method according to embodiment 5 to 7, wherein a toxicity grade is determined according to the following formula $$\frac{[EGF] \text{ drug substance} - [EGF] \text{ non-toxic reference} + (AW/100))}{[EGF] \text{ toxic reference} - [EGF] \text{ non-toxic reference} + (AW/100))} \times 100\%$$

9. The method according to any one of embodiments 2 to 8, wherein toxicity grade above 6 is predictive of nephrotoxicity of the drug substance, such as above 20, such as above 50.

10. The method according to any one of embodiments 1 to 9 wherein step d) further comprises the measurement of intracellular adenosine triphosphate (ATP) levels; wherein a decrease in intracellular ATP levels is indicative of a drug substance which is, or is predicted to be, associated with nephrotoxicity.

11. The method according to embodiment 10, wherein a level of intracellular ATP below 80% relative to the saline or non-toxic reference value is predicative of nephrotoxicity of the drug substance.

12. The method according to any one of embodiments 1 to 11, wherein step d) further comprises the measurement of extracellular kidney injury molecule-1 (KIM-1) protein or intracellular mRNA levels, wherein an increase in KIM-1 levels are indicative of a drug substance which is, or is predicted to be, associated with nephrotoxicity.

13. The method according to embodiment 12, wherein a level of above 200% relative to the saline or non-toxic reference value is predicative of nephrotoxicity of the drug substance.

14. The method according to any one of embodiment 1 to 13, wherein the cells expressing EGFR consume at least 50% EGF from the medium over 72 hours.

15. The method according to any one of embodiment 1 to 14, wherein the cells expressing EGFR is selected from the group consisting of epithelial cell, endothelial cell, mesenchymal cells, neuroectodermal cells and hepatocytes.

16. The method according to any one of embodiment 1 to 15, wherein the cells expressing EGFR is an epithelial cell culture or hepatocyte cell culture.

17. The method according to embodiment 16, wherein the cells are in the form of a primary cell culture selected from the group consisting of rodent primary cells, such as mouse or rat primary cells; pig (e.g. minipig) cells and primate primary cells, such as monkey (e.g. cynomolgus monkey) or human primary cells.

18. The method according to embodiment 17, wherein the primary cell culture is obtained from a rat or a human epithelial cells or hepatocytes.

19. The method according to embodiment 16 to 18, wherein the epithelial cell culture is a kidney epithelial cell culture or a lung epithelial cell culture.

20. The method according to embodiment 19, wherein the kidney epithelial cell is selected from the group consisting of proximal tubule epithelial cells, distal tubule epithelial cells and collecting duct epithelial cells.

21. The method according to any one of embodiments 19 or 20, wherein the cell culture is made from human PTEC or rat PTEC cells.

22. The method according to any one of embodiments 1 to 16 or 19 or 20, wherein the cells expressing EGFR are cultured from an immortalized cell line.

23. The method according to embodiment 22, wherein the cell line is not CACO2 or ARPE19.

24. The method according to embodiment 22, wherein cell culture is obtained from the group consisting of human PTEC-TERT-1, ciPTEC, HK-2, NKi-2 or human A549 cell lines.

25. The method according to any one of embodiments 1 to 24, wherein the cell culture media contains at between 5 and 15 ng/ml, such as between 8 and 15 ng/ml of epidermal growth factor (EGF), such as around 10 ng/ml.

26. The method according to any one of embodiments 1 to 24, wherein the period of incubation with the drug substance is between 2 and 6 days, such as around 3 days.

27. The method according to any one of embodiment 1 to 26, wherein the drug substance is selected from the group consisting of nucleic acid based molecules, chemotherapeutic agents; aminoglycosides; anti-bacterial agents, anti-viral agents; anti-fungal agents, anti-inflammatory agents and immunosuppressant agents.

28. The method according to any one of embodiments 1 to 27, wherein the drug substance is a nucleic acid molecule selected from a RNAi agents, an antisense oligonucleotide or an aptamer.

29. The method according to any one of embodiments 1 to 28, wherein the drug substance is an antisense oligonucleotide.

30. The method according to embodiment 29, wherein the oligonucleotide is administered to the cell culture in the absence of a transfection agent, i.e. by the process referred to as gymnosis.

31. The method according to embodiment 28, wherein the oligonucleotide is administered to the cell culture in the presence of a transfection agent.

32. The method according to any one of embodiments 28 to 31, wherein the nucleic acid molecule comprises one or more 2' sugar modified nucleosides.

33. The method according to embodiment 32, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

34. The method according to embodiment 32 or 33, wherein the one or more 2' sugar modified nucleoside is a LNA nucleoside.

35. The method according to embodiment 33 or 34, wherein the LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET, beta-D-ENA or alpha-L-ENA 36. The method according to any one of embodiments 28 to 35, wherein the nucleic acid molecule comprises at least one modified internucleoside linkage.

37. The method according to embodiment 36, wherein the internucleoside linkages within the contiguous nucleotide sequence are phosphorothioate internucleoside linkages.

38. The method according to any one of embodiments 28 to 37, wherein the antisense oligonucleotide is capable of recruiting RNase H.

39. The method according to embodiment 38, wherein the antisense oligonucleotide is a gapmer.

40. The method according to embodiment 38 or 39, wherein the oligonucleotide is a gapmer of formula 5'-F-G-F'-3', where region F and F' independently comprise 1-7 modified nucleosides and G is a region between 6 and 16 nucleosides which are capable of recruiting RNaseH.

41. The method according to embodiment 12 or 13, wherein the increase in KIM-1 is predicative of nephrotoxicity for a nucleic acid molecule according to any one of embodiments 28 to 40 even if the EGF levels are not increased.

42. The method according to any one of embodiments 1 to 40, wherein the in vivo nephrotoxicity is acute kidney injury and/or tubular degradation.

43. A method for selecting one or more drug substances for in vivo administration to a mammal, from a library of drug substances, said method comprising the steps of
 a. obtaining a library of drug substances;
 b. administering each member of the library of drug substances to a cell culture expressing epidermal growth factor receptor (EGFR) and where the medium contains at least 4 ng/ml of epidermal growth factor (EGF), such as per any one of embodiments 14 to 25;
 c. culturing the cells in vitro for a period of time, such as per embodiment 26;
 d. measuring the amount of intracellular EGF for each drug substance, such as per any one of the embodiments 1 to 13; and
 e. selecting one or more drug substances wherein the toxicity grade is below 6, when determined according to embodiment 8.

44. The method according to embodiment 43, wherein the therapeutic index of the selected drug substance is decreased when compared to a toxic reference substance or parent drug substance.

45. The method according to embodiment 43 or 44, wherein the library of drug substances is a library of nucleic acid molecules as per any one of embodiments 28 to 40.

46. The method according to embodiment 44, wherein the library of nucleic acid molecules is a library of nucleic acid molecule variants (child nucleic acid molecules) of a parent nucleic acid molecule, wherein the parent nucleic acid molecule is toxic, such as nephrotoxic, and wherein step d) identifies one or more nucleic acid molecule variants which are less toxic than the parent nucleic acid molecules; wherein the nucleic acid molecule variants retain the nucleobase sequence of the parent nucleic acid molecule.

47. The method according to anyone of embodiments 44 to 46, wherein the parent nucleic acid molecule is a nucleic acid molecule as per any one of embodiments 28 to 40, in particular an antisense oligonucleotide.

48. The method according to any one of embodiments 44 to 47, wherein the library of nucleic acid molecule variants comprises a population of child nucleic acid molecules which differ by virtue of the design from the parent nucleic acid molecule.

49. The method according to embodiment 44 to 48, wherein the nucleic acid molecule variants differ from the parent nucleic acid molecule in one or more design parameters selected from the group consisting of
 i. presence of one or more stereodefined phosphorothioate internucleoside linkages;
 ii. change in gap size;
 iii. introduction of a gap breaker;
 iv. change of wing size;
 v. change in 2' sugar modified nucleosides in the wings; and
 vi. mixed wing gapmers with at least two different 2' modified nucleosides in the wings, such as LNA nucleosides and 2' substituted nucleosides, in particular MOE.

50. The method according to embodiment 44 to 49, wherein the selection one or more drug substances for in vivo administration to a mammal is further based on results from an in vitro immunotoxicity assay and/or an in vitro hepatotoxicity assay which are suitable for predicting in vivo immunotoxicity and/or in vivo hepatotoxicity.

51. A drug substance obtained by the method according to any one of embodiments 43 to 50.

52. A pharmaceutical composition comprising the drug substance of embodiment 51 and a pharmaceutically acceptable diluent, solvent, carrier, salt and/or adjuvant.

53. The drug substance of embodiment 51 or the pharmaceutical composition of embodiment 52 for use in a medicine.

EXAMPLES

Methods and Materials
Compounds

TABLE 1 list of oligonucleotides used in the examples

| Comp ref | Target | Compound 5'→3' | SEQ ID NO | In vivo nephrotoxicity |
|---|---|---|---|---|
| 1-1 | Scramble | CGTcagtatgcgAATc | 1 | innocuous |
| 2-1 | PCSK9 | AATgctacaaaaCCCA | 2 | low |
| 3-1 | PCSK9 | TGCtacaaaacCCA | 3 | medium |
| 4-1 | PCSK9 | GCtgtgtgagcttGG | 4 | high |
| 5-1 | Myd88 | TAAggcaatcaagGTA | 5 | medium |
| 6-1 | Myd88 | CAAggaaacacaCAT | 6 | innocuous |
| 7-1 | Myd88 | CAAatgctgaaacTAT | 7 | innocuous |
| 8-1 | Myd88 | ACTgctttccactCTG | 8 | high |
| 8-2 | Myd88 | ACTgc$_s$tttc$_s$cac$_s$tCTG | 8 | n.d |
| 8-3 | Myd88 | ACTgc$_r$tttc$_r$cac$_r$tCTG | 8 | n.d |
| 9-1 | Myd88 | GCCtcccagttccTTT | 9 | low/medium |

TABLE 1-continued list of oligonucleotides used in the examples

| Comp ref | Target | Compound 5'→3' | SEQ ID NO | In vivo nephrotoxicity |
|---|---|---|---|---|
| 10-1 | Myd88 | CACattccttgctCTG | 10 | medium |
| 10-2 | Myd88 | CACatt$_s$cctt$_s$gct$_s$CT$_s$G | 10 | n.d |
| 10-3 | Myd88 | CACatt$_r$cctt$_r$gct$_r$CT$_r$G | 10 | n.d |
| 10-4 | Myd88 | CACatt$_s$c$_s$ctt$_s$g$_s$ctCTG | 10 | n.d |
| 10-5 | Myd88 | CACatt$_r$c$_r$ctt$_r$g$_r$ctCTG | 10 | n.d |
| 11-1 | Myd88 | TGCtcaacatcAAG | 11 | medium |
| 12-1 | Myd88 | TTAacttgacCCA | 12 | high |
| 13-1 | Myd88 | TTTacacttgaCCC | 13 | medium |
| 14-1 | Myd88 | GTCagaaacaaccACC | 14 | high |
| 15-1 | BCL11A | CTAtgtgttccTGT | 15 | medium/high |
| 16-1 | BCL11A | CGTttgtgctcgaTAA | 16 | medium/high |
| 17-1 | BCL11A | CGTttgtgctcgATA | 17 | high |
| 18-1 | BCL11A | ATTgcattgtttcCGT | 18 | low |
| 19-1 | BCL11A | CATtgcattgtttCCG | 19 | low/medium |
| 19-2 | BCL11A | CATtgcattgttTCCG | 19 | high |
| 20-1 | SGLT2 | *gg*catgagct*tc* | 20 | low/medium |

For the compounds lower case letters represent DNA units, case letters represent beta-D-oxy-LNA units. All LNA C units are 5' methyl C and all internucleoside linkages are phosphorothioate linkage. Rp stereodefined phosphorothioate linkage are indicated by subscript r. Sp stereodefined phosphorothioate linkage are indicated by subscript s. Bold, italic lower case letters represent MOE units. In compound 20-1 all C units (DNA and MOE) are 5' methyl C. The SEQ ID NO refers to the nucleobase sequence of the compound.

Measuring In Vivo Nephrotoxicity

Purpose bred Wistar Han Crl:WI(Han) male rats obtained from Charles River Laboratories at 7 to 8 weeks of age were divided into groups of 4 (table 1, exp. A) or 8 (table 1, exp. B) based on body weight and acclimatized for at least 5 days before dosing. The animals were housed under standard environmental conditions (22±20° C., relative humidity 50±20%, a light/dark cycle 12 h/12 h, pelleted food and water ad libitum), were offered enriched environment in an AAALAC accredited facility and were regularly and carefully monitored. All procedures were in accordance with the respective local regulations and according to the animal permissions granted by the Institutional Animal Care and Use Committee. Test compounds were formulated in isotonic sterile saline, sterile filtered (0.22 µm), and dosed at 40 mg/kg on days 1 and 8 (2.5 ml/kg) in the intrascapular region. Control group animals received saline as vehicle control. On day 15 animals were orally administered tap water (10 ml/kg), and urine was collected on ice for 6 hours in metabolic cages. Urine protein levels (Aution Max AX-4280) and urinary renal injury biomarkers were measured (Multiplex MAP Rat Kidney Toxicity Magnetic Bead Panel 2). On day 15 the rats were sacrificed by an intraperitoneal injection of pentobarbital and exsanguinated. Kidney cortex samples were collected and fixed by immersion in 10% neutral buffered formalin, embedded in paraffin, sectioned to 5 µm and stained with hematoxylin and eosin (H&). The H&E sections were then scanned at 20× magnification using an Aperio ScanScope AT™ (Leica Biosystems) scanner and pictures were then captured via ImageScope™ software from the scanned images. One or more of the following parameters were assessed kidney weight, serum creatinine, urine protein, KIM-1 protein in urine, KIM-1 mRNA, kidney degeneration/regeneration and relative tubulotoxicity grade.

Cell Cultures

Human primary proximal tubule epithelial cells (PTEC) cell culture Primary PTEC (Science Cell Research Labotories catalog #4100) were cultured according to the manufacturer's instructions in PTEC medium [DMEM/F12 without phenol red (ThermoFisher Scientific 11039021) containing 1% Penicillin-Streptomycin solution (ThermoFisher Scientific 15140122), 10 mM HEPES (ThermoFisher Scientific 15630056), 5 ug/ml insulin and 5 ug/ml transferrin and 8.65 ng/ml sodium selenite (all from a 100× concentrated stock solution, ThermoFisher Scientific 41400045), 100 nM hydrocortisone (Sigma H6909), 3.5 ug/ml ascorbic acid (Sigma A4403), 25 ng/ml prostaglandin E1 (Sigma P5516), 3.25 µg/ml triiodo-L-thyronine (Sigma T6397), 10 ng/ml human recombinant epidermal growth factor (EGF, R&D Systems 236-EG-200), and 100 µg/ml Geneticin (G418 sulfate, ThermoFisher Scientific 10131027)].

Prior to treatment with oligonucleotides the primary PTEC cells were seeded into collagen I-coated 96-well plates (Corning, 356407) at a density of 40 000 and 20 000 cells/well respectively in PTEC medium and grown until confluence.

Human PTEC-TERT1 Cell Culture

PTEC-TERT1 (Evercyte GmbH, Austria) were cultured according to the manufacturer's instructions in PTEC medium [DMEM/F12 without phenol red (ThermoFisher Scientific 11039021) containing 1% Penicillin-Streptomycin solution (ThermoFisher Scientific 15140122), 10 mM HEPES (ThermoFisher Scientific 15630056), 5 ug/ml insulin and 5 ug/ml transferrin and 8.65 ng/ml sodium selenite (all from a 100× concentrated stock solution, ThermoFisher Scientific 41400045), 100 nM hydrocortisone (Sigma H6909), 3.5 ug/ml ascorbic acid (Sigma A4403), 25 ng/ml prostaglandin E1 (Sigma P5516), 3.25 pg/ml triiodo-L-thyronine (Sigma T6397), 10 ng/ml human recombinant epidermal growth factor (EGF, R&D Systems 236-EG-200), and 100 µg/ml Geneticin (G418 sulfate, ThermoFisher Scientific 10131027)].

Prior to treatment with oligonucleotides the PTEC-TERT1 were seeded into collagen I-coated 96-well plates (Corning, 356407) at a density of 40 000 and 20 000 cells/well respectively in PTEC medium and grown until confluence.

Rat Primary Proximal Tubule Epithelial Cells (PTEC) Cell Culture

Proximal renal tubule epithelial cells were prepared by a simplified procedure of that described by Bruce et al, Methods Mol Biol 1001, 53-64 (2013). Kidneys were removed from one anesthetized male Wistar rat (age: 10-18 weeks) and were washed in cold 1× concentrated Hanks balanced salt solution (HBSS, ThermoFisher Scientific 14065049). The organs were decapsulated, and the outer stripes of the kidney cortex without medulla were cut into 1 to 2 mm$^3$ pieces. Tissue pieces were digested in 25 ml of HBSS containing 2 mg/ml collagenase A (Roche 10103586001) and 10 ug/ml DNAse I (Roche 10104159001) at 37° C. for 60 min. with continuous gentle shaking. The reaction was stopped by addition of 25 ml of ice-cold HBSS containing 2% bovine serum albumin (BSA, Fraction V, Roche 10735086001). Dissociated tissue was filtered consecutively first through a 200 µm cell strainer (pluriSelect 43-50200) and subsequently through a 100 um cell strainer (PluriSelect™ 43-50100); the filtrate containing single cells and tubule fragments was washed and centrifuged three times (100 g) in HBSS solution without MgCl2 and CaCl2) (HBSS–/–, ThermoFisher Scientific 14175053). The sediment was resuspended in 25 ml HBSS–/– and mixed with 25 ml of 30% OptiPrep solution [mixture of 5 volumes of 60% OptiPrep™ density gradient media (Sigma D1556), 4 volumes of H2O sterile, and 1 volume of 10× concentrated phosphate buffered saline without MgCl2 and CaCl2) (PBS–/– ThermoFisher Scientific 14200-067) to obtain a suspension of cells and tubular fragments in 15% OptiPrep™. The suspension was centrifuged (800 g, at room temperature for 20 min). The cell band in the upper third of the tube was harvested; cells in the sediment at the bottom of the tube were discarded. Harvested cells were washed and centrifuged three times (400 g, at room temperature for 5 min.) in rat PTEC medium [1 volume DMEM (ThermoFisher Scientific 11966025), 1 volume Ham's F-12 nutrient mix (ThermoFisher Scientific 21765029), 2% fetal bovine serum (FBS, ThermoFisher Scientific 16000044), 1% Penicillin-Streptomycin solution (ThermoFisher Scientific 15140122), 10 mM HEPES (ThermoFisher Scientific 15630056), 5 ug/ml insulin and 5 ug/ml transferrin and 8.65 ng/ml sodium selenite (all from a 100× concentrated stock solution, ThermoFisher Scientific 41400045), 100 nM hydrocortisone (Sigma H6909), 3.5 ug/ml ascorbic acid (Sigma A4403), 25 ng/ml prostaglandin E1 (Sigma P5516), 3.25 pg/ml triiodo-L-thyronine (Sigma T6397), and 10 ng/ml rat recombinant epidermal growth factor (EGF, R&D Systems 3214-EG-100/CF)]. After the final centrifugation step, the cell preparation was resuspended in 50 ml of rat PTEC medium and distributed into three collagen I-coated 150 cm$^2$ cell culture flasks (Corning 354486) followed by incubation for 4 days with a change of medium after the first 2 days.

Prior to treatment with oligonucleotides the expanded rat PTEC cells were harvested from the culture flasks by detachment with trypsin-EDTA solution (ThermoFisher Scientific 25200056), washed in rat PTEC medium and seeded into collagen I-coated 96 well plates (Corning, 356407) at a density of 36 000 cells/well in rat PTEC medium for growth until confluence.

Primary Human Hepatocytes

Cryopreserved human hepatocytes were suspended in William's Medium E (WME) without phenol red (Sigma W-1878) supplemented with 10% fetal calf serum, penicillin (100 U/ml), streptomycin (0.1 mg/ml) at a density of approx. 1×10$^6$ cells/ml and seeded into collagen-coated 96-well plates (Becton Dickinson AG, Allschwil, Switzerland) at a density of 0.4×10$^5$ cells/well. Cells were pre-cultured for 3 to 4 h allowing for attachment to cell culture plates before start of treatment with oligonucleotides.

Before oligonucleotide treatment the seeding medium was replaced by 90 µl of serum free WME.

A549 Cells (Adenocarcinomic Human Alveolar Basal Epithelial Cells)

A549 cells (ATCC CCL-185) were cultivated according to the manufacturer's instructions in A549 medium [F-12K Nut Mix (Gibco, 21127-022), 1% penicillin/streptomycin (Gibco: 15140-122), 10% FBS (Gibco 16000-044)].

Prior to treatment with oligonucleotides the A549 cells were seeded in 96 well plates at 3'000 cells per well in A549 regular medium and grown until 60% confluence.

For lipofection, cells were transfected with 1 or 10 ng of oligonucleotide using Lipofectamin® (Invitrogen, 11668-019) according to the manufacturer's instructions. After 24 hours the medium was changed for A549 regular medium containing 10 ng/ml EGF and 2% FCS. After 72 hours the cells were harvested and ATP was measured and the supernatant was stored at −20° C. for EGF analysis.

Oligonucleotide Treatment Using Gymnosis

Oligonucleotides were dissolved in PBS and added to the cell culture at the given concentration, such as 10, 30 or 100 µM. The total volume of each well was 100 µl. PBS served as vehicle control.

When intracellular ATP was to be analyzed following the oligonucleotide treatment the medium was changed every 3 days including addition of the same concentration of oligonucleotide as day 0.

When extra cellular markers, like EGF and KIM-1, were analyzed following the oligonucleotide treatment the medium was collected and stored at −20° C. until further analysis. Cells that were grown beyond 3 days of the first oligonucleotide treatment had the medium collected and replaced every 3 days incl. fresh oligonucleotide. The collected medium was stored at −20° C.

ATP Assay

For the determination of intracellular ATP levels the CellTiter-Glo® Luminescent Cell Viability Assay (G7571, Promega Corporation, Madison Wis., USA) was used according to the manufacturer's instructions. Each sample was tested in triplicate. Unless indicated otherwise the intracellular ATP levels were measured at day 9 after oligonucleotide treatment.

EGF Assay

For analysis of human EGF, cell supernatants were thawed on ice, diluted 1:2 and 1:10 in sample dilution buffer (BioRad catalog # M60-009RDPD) and analyzed by Luminex®-based ELISA using human EGF beads (Bio-Plex Pro™ Human Cancer Biomarker Panel 2 EGF Set#171BC603M), or followed by analysis using the Bio-Plex® 200 Systems (BioRad) according to the manufacturer's instructions. Data are reported as mean concentrations and standard deviations of triplicate wells. An increase of EGF levels above 200% was considered as predictive for nephrotoxicity.

KIM-1 Assay

For analysis of human KIM-1, cell supernatants were thawed on ice, diluted 1:2 and 1:10 in sample dilution buffer (BioRad catalog # M60-009RDPD) and analyzed by Luminex®-based ELISA using human KIM-1 beads (Human Kidney Injury panel 4, Millipore HKI4MAG-99K-KIM1) followed by analysis using the Bio-Plex® 200 Systems (BioRad) according to the manufacturer's instructions. Data are reported as mean concentrations and standard deviations of triplicate wells. An increase of KIM-1 levels above 200% was considered as predictive for nephrotoxicity.

Example 1 Morphological Changes of Cell Cultures Upon Oligonucleotide Treatment

The present example evaluates the effect on the morphology of a cell culture following oligonucleotide treatment.

PTEC-TERT1 cells were cultures as described in the "Materials and methods" section. To mimic the physiological exposure of renal tubules to circulating naked oligonucleotide (i.e. without assistance of delivery technology, herein termed gymnosis or gymnotic delivery), confluent monolayers of PTEC-TERT1 cells were exposed to an aqueous solution of 100 µM oligonucleotide. The medium was replaced every three days including 100 µM fresh oligonucleotide in the fresh medium.

After 7 days of treatment the morphological alterations in the treated cell cultures were investigated under bright field microscopy. FIG. 1 show that PTEC-TERT1 cells treated with oligonucleotide compound 1-1 (innocuous in vivo) did not show any morphological changes compared to saline treated cells. Cells treated with oligonucleotide compound 3-1 (medium in vivo tox) formed irregular domes and vacuoles whereas PTEC-TERT1 cells treated with oligonucleotide compound 4-1 (high in vivo tox) adopted a flattened and stable appearance.

Both the toxic compounds show morphological changes, however the less toxic compound 3-1 produce more significant morphological changes than the highly toxic compound 4-1.

In conclusion toxic oligonucleotides affect the morphology, the severity of the toxicity can however not be predicted using morphological changes.

Example 2 Oligonucleotide Effects on Extracellular EGF in PTEC and PTEC-TERT1 Cells The present example evaluates the effect on the soluble biomarker, EGF, in the cell culture medium after exposure of oligonucleotides.

The primary PTEC cells and immortalized PTEC-TERT-1 cell line were cultured according to the conditions described in the "Materials and methods" section. At confluence the cells were treated with oligonucleotide as described in the "Materials and methods" section, in concentrations of 3, 10, 30 or 100 µM.

The EGF concentration in the medium was measured according to the EGF assay in the "Materials and methods" section.

The results are shown in tables 2 below and represent the average of three identical treatments.

TABLE 2

EGF concentration 3 or 6 days after oligonucleotide treatment.

| | | | PTEC | | | | PTEC-TERT1 | | | |
|---|---|---|---|---|---|---|---|---|---|---|
| | | | Day 3 | | Day 6 | | Day 3 | | Day 6 | |
| In vivo tox | Comp # | Conc µM | EGF % saline | SD | EGF % saline | SD | EGF % saline | SD | EGF % saline | SD |
| | saline | 0 | 100 | 6 | 100 | 14 | 100 | 3 | 100 | 2 |
| Innocuous | 1-1 | 3 | 95 | 7 | 62 | 6 | 88 | 3 | 124 | 1 |
| | | 10 | 99 | 20 | 71 | 5 | 93 | 4 | 152 | 0.8 |
| | | 30 | 112 | 5 | 77 | 4 | 108 | 4 | 180 | 4 |
| | | 100 | 120 | 13 | 98 | 5 | 119 | 3 | 172 | 3 |
| Medium | 3-1 | 3 | 114 | 22 | 152 | 28 | 70 | 5 | 124 | 1 |
| | | 10 | 139 | 19 | 286 | 11 | 75 | 17 | 137 | 2 |
| | | 30 | 134 | 16 | 653 | 116 | 70 | 13 | 231 | 4 |
| | | 100 | 269 | 60 | 915 | 55 | 128 | 12 | 2413 | 22 |
| high | 4-1 | 3 | 198 | 25 | 525 | 57 | 71 | 4 | 37 | 3 |
| | | 10 | 323 | 67 | 1171 | 145 | 116 | 5 | 222 | 28 |
| | | 30 | 373 | 46 | 1588 | 316 | 302 | 9 | 8398 | 25 |
| | | 100 | 631 | 92 | 1403 | 223 | 1572 | 4 | 8899 | 612 |

From this it can be seen that already at day 3 in primary PTEC cells, the toxic oligonucleotides (compound 3-1 and 4-1) show a significant increase in soluble EGF in the medium at the 100 µM oligonucleotide concentration when compared to saline as well as the innocuous compound 1-1. At day 6 it is possible to detect the toxic compound down to a concentration of 10 µM in primary PTEC cells, whereas 100 µM is need in PTEC-TERT1 cells. Furthermore, it is possible to differentiate the severity of the toxicity that was observed in vivo for these compounds both at day 6 in both cell lines. PTEC-TERT1 cells consist of human proximal tubular cells immortalized through stable expression of the catalytic subunit of human telomerase reverse transcriptase (TERT). PTEC-TERT1 were developed as a cell model that maintains morphological and functional properties of primary PTEC cells with an additional replicative advantage over primary cells that have a finite lifespan in vitro due to telomere shortening.

Example 3 Oligonucleotide Effects on Extracellular EGF in PTEC-TERT1 Cells

The present example evaluates whether EGF as biomarker in immortalized PTEC-TERT1 cells can be used to differentiate the grades of toxicity observed in vivo using one innocuous oligonucleotides and 4 oligonucleotides with different in vivo grade of toxicity.

The immortalized PTEC-TERT-1 cell line was cultured according to the conditions described in the "Materials and methods" section. At confluence the cells were treated with oligonucleotide as described in the "Materials and methods" section, in concentrations of 3, 10, 30 or 100 µM.

The EGF concentrations were measured at day 3, 7 and day 10 after treatment according to the EGF assay in the "Materials and methods" section.

The results are shown in tables 3 below, and represent the average of three identical treatments.

TABLE 3

EGF concentration 3, 7 and 10 days after oligonucleotide treatment.

| In vivo grade of toxicity | Comp # | Conc µM | Day 3 EGF % saline | SD | Day 7 EGF % saline | SD | Day 10 EGF % saline | SD |
|---|---|---|---|---|---|---|---|---|
| | saline | 0 | 100 | 20 | 100 | 20 | 100 | 56 |
| Innocuous | 1-1 | 11 | 145 | 28 | 94 | 12 | 32 | 2 |
| | | 33 | 214 | 20 | 122 | 29 | 41 | 9 |
| | | 100 | 137 | 27 | 135 | 15 | 59 | 17 |
| Low | 2-1 | 11 | 135 | 17 | 69 | 11 | 47 | 10 |
| | | 33 | 192 | 23 | 88 | 18 | 63 | 27 |
| | | 100 | 172 | 23 | 117 | 17 | 154 | 39 |
| Medium | 3-1 | 11 | 151 | 30 | 168 | 21 | 41 | 3 |
| | | 33 | 213 | 62 | 287 | 9 | 138 | 15 |
| | | 100 | 207 | 39 | 493 | 58 | 227 | 22 |
| High | 4-1 | 11 | 225 | 49 | 637 | 33 | 1177 | 211 |
| | | 33 | 368 | 19 | 983 | 59 | 1865 | 0 |
| | | 100 | 484 | 52 | 983 | 126 | 1792 | 0 |
| Medium | 5-1 | 11 | 174 | 8 | 158 | 16 | 54 | 1 |
| | | 33 | 222 | 32 | 249 | 41 | 210 | 48 |
| | | 100 | 182 | 30 | 754 | 49 | 720 | 63 |

From this it can be seen that at day 3 the highly toxic compound (compound 4-1) show a significant increase in soluble EGF in the medium when dosed at 33 or 100 µM, when compared to the other compounds. At day 7 it is possible to detect the medium and highly toxic compound down to a concentration of 33 µM, and the severity of the toxicity among the compounds can be differentiated at 100 µM oligonucleotide. At day 10 it is more difficult to differentiate the medium toxic oligonucleotide (compound 3-1) from the low toxic oligonucleotide (compound 2-1). Both do however differentiate from the innocuous oligonucleotide (Compound 1-1), the more toxic compound 4-1 and 5-1 still differentiate well at day 10 when dosed at 100 µM.

Example 4 Oligonucleotide Effects on Extracellular EGF in PTEC-TERT1 Cells

The present example evaluates whether the findings in example 3 can be reproduced for a larger set of oligonucleotides directed to other targets. In the same study two other biomarkers KIM-1 and intracellular ATP was measured as well.

The immortalized PTEC-TERT-1 cell line was cultured according to the conditions described in the "Materials and methods" section. At confluence the cells were treated with oligonucleotide as described in the "Materials and methods" section, in concentrations of 10, 30 or 100 µM.

EGF and KIM-1 measurements were performed at day 6. For ATP measurements the cells were harvested at day 9 after oligonucleotide treatment. EGF, KIM-1 and ATP concentrations were measured according to the assays described in the "Materials and methods" section.

The results are shown in tables 4 below, and represent the average of three identical treatments.

TABLE 4

EGF and KIM-1 levels in culture media at day 6, intracellular ATP levels at day 9 after oligonucleotide treatment.

| In vivo grade of toxicity | Comp # | Conc µM | Day 6 EGF % saline | SD | Day 6 KIM-1 % saline | SD | Day 9 ATP % saline | SD |
|---|---|---|---|---|---|---|---|---|
| Innocuous | 6-1 | 10 | 78 | 5 | 140 | 13 | 93 | 4 |
| | | 30 | 90 | 7 | 150 | 6 | 99 | 3 |
| | | 100 | 118 | 10 | 122 | 8 | 101 | 3 |
| Innocuous | 7-1 | 10 | 37 | 3 | 159 | 4 | 113 | 7 |
| | | 30 | 40 | 0 | 127 | 3 | 114 | 6 |
| | | 100 | 67 | 14 | 120 | 6 | 107 | 1 |
| High | 8-1 | 10 | 1153 | 47 | 78 | 29 | 59 | 3 |
| | | 30 | 1359 | 125 | 63 | 1 | 47 | 7 |
| | | 100 | 1545 | 58 | 54 | 1 | 43 | 1 |
| Medium | 9-1 | 10 | 220 | 65 | 151 | 7 | 99 | 2 |
| | | 30 | 284 | 62 | 129 | 8 | 101 | 2 |
| | | 100 | 1593 | 180 | 116 | 29 | 103 | 4 |
| Medium | 10-1 | 10 | 73 | 28 | 123 | 17 | 87 | 2 |
| | | 30 | 330 | 102 | 77 | 1 | 66 | 6 |
| | | 100 | 783 | 21 | 65 | 4 | 60 | 5 |
| Medium | 11-1 | 10 | 38 | 5 | 149 | 13 | 136 | 2 |
| | | 30 | 127 | 34 | 111 | 10 | 135 | 6 |
| | | 100 | 371 | 42 | 82 | 8 | 119 | 4 |
| High | 12-1 | 10 | 19 | 2 | 325 | 37 | 132 | 2 |
| | | 30 | 27 | 4 | 379 | 20 | 133 | 1 |
| | | 100 | 71 | 5 | 289 | 26 | 90 | 4 |
| Medium | 13-1 | 10 | 27 | 2 | 268 | 46 | 124 | 10 |
| | | 30 | 29 | 2 | 242 | 51 | 122 | 5 |
| | | 100 | 39 | 0 | 252 | 17 | 114 | 2 |
| Medium | 15-1 | 10 | 38 | 7 | 43 | 3 | 101 | 2 |
| | | 30 | 76 | 11 | 34 | 3 | 92 | 0 |
| | | 100 | 234 | 43 | 25 | 2 | 52 | 2 |
| Mild tox | 18-1 | 10 | 223 | 21 | 188 | 17 | 121 | 1 |
| | | 30 | 203 | 31 | 193 | 21 | 112 | 4 |
| | | 100 | 290 | 47 | 181 | 13 | 105 | 0 |
| Mild tox | 19-1 | 10 | 317 | 54 | 120 | 11 | 100 | 2 |
| | | 30 | 310 | 18 | 129 | 24 | 90 | 2 |
| | | 100 | 413 | 31 | 77 | 15 | 76 | 1 |
| Medium | 16-1 | 10 | 394 | 29 | 160 | 10 | 123 | 1 |
| | | 30 | 509 | 56 | 164 | 15 | 122 | 1 |
| | | 100 | 707 | 81 | 129 | 16 | 113 | 0 |
| High | 19-2 | 10 | 370 | 71 | 75 | 11 | 67 | 1 |
| | | 30 | 606 | 52 | 57 | 16 | 54 | 2 |
| | | 100 | 770 | 67 | 28 | 4 | 40 | 1 |
| High | 17-1 | 10 | 342 | 48 | 167 | 20 | 124 | 1 |
| | | 30 | 550 | 16 | 202 | 4 | 116 | 2 |
| | | 100 | 693 | 42 | 140 | 23 | 96 | 1 |

From table 4 it can be seen that the EGF biomarker is capable of predicting 10 out of 12 toxic compounds at the 100 µM oligonucleotide dose.

KIM-1 only predicts 2 out of the 12 toxic compounds, however these are the compounds that were not caught be the EGF biomarker, indicating that KIM-1 can supplement the predictions made with EGF as biomarker.

ATP as biomarker is capable of predicting 5 of the 12 toxic compounds. Consequently, the ATP biomarker can be used to supplement the EGF biomarker but it is not as predictive as the EGF biomarker.

The results are also summarized in FIG. 2.

Example 5 Oligonucleotide Effects on Extracellular EGF in Primary Hepatocytes

In the following example it was investigated whether non-renal cells expressing functional EGFR can be used to predict nephrotoxicity of an oligonucleotide.

Human primary hepatocytes were cultivated as described in the "Materials and methods" section with addition of 10 ng/ml of EGF to the medium. At confluence the cells were treated with oligonucleotide as described in the "Materials and methods" section, in concentrations of 10 or 100 µM.

The medium was obtained at day 3, and the EGF level was measured according to the assay described in the "Materials and methods" section.

The results are shown in tables 5 below, and represent the average of three identical treatments.

TABLE 5

EGF levels in culture media from primary hepatocytes at day 3 after oligonucleotide treatment.

| In vivo grade of toxicity | Comp # | Conc µM | EGF % saline | SD |
|---|---|---|---|---|
| | saline | 0 | 100 | 8 |
| Innocuous | 1-1 | 10 | 123 | 27 |
| | | 100 | 159 | 19 |
| low | 2-1 | 10 | 122 | 41 |
| | | 100 | 211 | 51 |
| Innocuous | 14-1 | 10 | 139 | 32 |
| | | 100 | 220 | 37 |
| Medium | 3-1 | 10 | 227 | 34 |
| | | 100 | 411 | 100 |
| High | 4-1 | 10 | 323 | 62 |
| | | 100 | 985 | 175 |
| Medium | 10-1 | 10 | 145 | 16 |
| | | 100 | 574 | 50 |
| Medium | 11-1 | 10 | 184 | 25 |
| | | 100 | 458 | 21 |

From this it can be seen that at 100 µM oligonucleotide all the nephrotoxic compounds can be identified using primary hepatocytes, and the severely toxic compound (4-1) can be differentiated from the more moderately toxic compounds.

Example 6 Oligonucleotide Effects on Extracellular EGF in Transfected Cells

In this example it was tested whether cell lines that are more suitable for transfection with oligonucleotide than for gymnosis could be applied in the method of predicting nephrotoxicity.

A549 were cultivated as described in the "Materials and methods" section. At after at 50-60% confluence the oligonucleotides were transfected into the cells using 0.5 µl Lipofectamin (Invitrogen, 11668-019) in 25 µl OptiMEM® (GIBCO 31985062) and 1 ng or 10 ng oligonucleotide in the same volume OptiMEM. The cells were incubated over night at 37° C. The medium was changed using A459 regular medium+10 ng/ml EGF. 48 hours after transfection the medium was collected for EGF measurements and the cells were harvested for ATP measurements.

The results are shown in tables 6 below, and represent the average of three identical treatments.

TABLE 6

EGF and ATP levels from A549 cells 48 hours after transfection with oligonucleotide

| In vivo grade of toxicity | Comp # | Conc ng | EGF % saline | SD | ATP % saline | SD |
|---|---|---|---|---|---|---|
| | saline | 0 | 100 | 14 | 100 | 5 |
| Innocuous | 1-1 | 1 | 69 | 1 | 89 | 8 |
| | | 10 | 75 | 9 | 100 | 12 |
| low | 2-1 | 1 | 80 | 1 | 96 | 6 |
| | | 10 | 161 | 5 | 59 | 4 |
| Medium | 3-1 | 1 | 99 | 9 | 91 | 3 |
| | | 10 | 199 | 7 | 44 | 2 |
| High | 4-1 | 1 | 132 | 34 | 93 | 3 |
| | | 10 | 211 | 9 | 51 | 7 |
| High tox | 8-1 | 1 | 140 | 33 | 101 | 3 |
| | | 10 | 233 | 12 | 58 | 4 |

These data show that EGF can also be used as a biomarker for nephrotoxicity in transfected epithelial cells. The oligonucleotides with high toxicity (4-1 and 8-1) are already detectable at 1 ng, whereas the medium toxic oligonucleotide (3-1) needs 10 ng.

The data also show that ATP can be used as a biomarker for nephrotoxicity in transfected epithelial cells at a dose of 10 ng oligonucleotide.

The innocuous oligonucleotide (2-1) show signs of falls toxicity both with EGF and ATP as biomarker when transfected with 10 ng oligonucleotide. Potentially a concentration between 1 and 10 ng, such as 5 ng may be more suitable.

Example 7: Effects on Extracellular EGF in Cells Treated with Design Variants of a Parent Oligonucleotide In the present example a small library of oligonucleotide variants that have the same nucleotide sequence as the parent compound but have different design, in this case fixed stereo chemistry at give positions, were screened to select an oligonucleotide variant with less toxicity than the parent compound. The parent oligonucleotides were known to elicit medium toxicity (compound 10-1) or high toxicity (compound 8-1) when tested in vivo.

The immortalized PTEC-TERT-1 cell line was cultured according to the conditions described in the "Materials and methods" section. At confluence the cells were treated with oligonucleotide as described in the "Materials and methods" section, in concentrations of 10 or 30 µM.

EGF levels were measured at day 6 after treatment according to the assays described in the "Materials and methods" section.

The results are shown in tables 7 below, and represent the average of three identical treatments. The toxicity grade was calculated according to the following formula:

$$\left( \frac{[EGF] \text{ drug substance} - [EGF] \text{ saline reference} + (AW/100))}{[EGF] \text{ toxic reference} - [EGF] \text{ saline reference} + (AW/100))} \times 100\% \right)$$

Where AW is the assay window determined as the difference between the saline reference and the nephrotoxic reference compound 4-1 (i.e. AW=saline−toxic reference).

TABLE 7

EGF levels of a library of chirally modified oligonucleotides after 6 days in PTEC-TERT1 cells.

| | | 10 µM oligonucleotide | | | 30 µM oligonucleotide | | |
|---|---|---|---|---|---|---|---|
| | Comp # | EGF % saline | SD | Toxicity grade | EGF % saline | SD | Toxicity grade |
| | saline | 100 | 9 | | 100 | 7 | |
| Parent | 10-1 | 305 | 58 | 11 | 1283 | 650 | 17 |
| Chiral variant Sp | 10-2 | 93 | 13 | 3 | 156 | 47 | 1 |
| Chiral variant Rp | 10-3 | 248 | 95 | 9 | 1740 | 669 | 23 |
| Chiral variant Sp | 10-4 | 60 | 2 | 1 | 157 | 82 | 1 |
| Chiral variant Rp | 10-5 | 369 | 125 | 13 | 1069 | 360 | 14 |
| Parent | 8-1 | 8412 | 1905 | 323 | 15126 | 1182 | 208 |
| Chiral variant Sp | 8-2 | 5723 | 160 | 219 | 25199 | 1067 | 347 |
| Chiral variant Rp | 8-3 | 869 | 65 | 32 | 3416 | 160 | 46 |
| Toxic reference | 4-1 | 2622 | 855 | 100 | 7311 | 143 | 100 |

From these data it can be seen that with the present assay it is possible to screen a library of oligonucleotide variants and identify compound which have a significant reduction in the toxicity grade when compared to the parent molecule. In particular compounds 10-2 and 10-4 are suitable candidates for further in vivo tests.

Example 8 EGF Consumption in PTEC-TERT-1 Cells

The present example investigated how EGF is consumed in PTEC-TERT1 cells and also investigated the effect of EGF in the medium in the prediction of oligonucleotides toxicity.

The EGF consumption from the medium of non-treated PTEC-TERT1 cells after 72 hours after adding 10 ng EGF/ml of medium to the cells is shown in Table 8, and clearly shows that the non-treated PTEC-TERT1 cells consume the EGF in the medium over time.

TABLE 8

EGF consumption in PTEC-TERT1 cells

| Time/h | 0 | 8 | 24 | 48 | 72 |
|---|---|---|---|---|---|
| EGF in Supernatant (pg/ml) | 10000 | 9273 ± 662 | 8859 ± 1117 | 5407 ± 613 | 1280 ± 470 |

Example 9 Relevance of EGF in the Medium

The relevance of adding EGF to the culture medium when assessing the toxicity of an oligonucleotide was assessed by cultivating PTEC-TERT1 cells as described in the "Materials and methods" section and treating the cells at confluence with 25 or 100 µM oligonucleotide for 6 days either in the presence (10 ng/ml) or absence of EGF in the medium. The results are shown in Table 9 and represent the average of three identical treatments.

TABLE 9

Effect of EGF in the medium when assessing oligonucleotide toxicity

| In vivo grade of toxicity | Comp# | Conc µM | No EGF in Medium | | 10 ng/ml EGF in medium | |
|---|---|---|---|---|---|---|
| | | | EGF pg/ml | SD | EGF pg/ml | SD |
| | Saline | | 3.9 | 0.7 | 188.9 | 15.7 |
| Medium | 3-1 | 25 | 6.3 | 2.0 | 245.0 | 30.3 |
| | | 100 | 12.2 | 0.7 | 341.8 | 37.1 |
| High | 4-1 | 25 | 5.4 | 6.5 | 731.7 | 223.3 |
| | | 100 | 5.3 | 12.0 | 1957.8 | 188.2 |

From this it can be seen that when no EGF is present in the medium it is not possible to see effects on EGF levels in the medium upon treatment with toxic oligonucleotides. On the other hand when 10 ng/ml EGF is present in the medium the EGF levels in the cells treated with toxic oligonucleotides are clearly increased in the medium indicating that the EGF consumption of the cells are impaired due to the oligonucleotide treatment.

To confirm that it is an impairment of the consumption (uptake of EGF into the cells) and not a reduction in EGF expression by the cells, the mRNA level of EGF in the cells was measured and clearly showed that the cells do not express EGF.

Example 10 Investigation of EGF Concentrations in the Medium

As seen in example 9, the presence of some EGF in the medium is needed to get nephrotoxicity readout in the assay. The present example evaluates the effect of the EGF concentration in the culture medium on the intracellular ATP levels as well as on the target knockdown by the oligonucleotides.

Intracellular ATP level was measured in confluent PTEC-TERT1 after 9 days exposure to 100 µM oligonucleotide along with 0, 1, 3, 10, 30 and 100 ng/ml of EGF in the medium. The results are shown in table 10, and represent the average of three identical treatments.

TABLE 10

Intracellular ATP as % of saline with varying levels of EGF in the medium

| | EGF ng/ml | | | | | | | | | | | |
|---|---|---|---|---|---|---|---|---|---|---|---|---|
| | 0 | | 1 | | 3 | | 10 | | 30 | | 90 | |
| Comp # | ATP | SD | ATP | SD | ATP | SD | ATP | SD | ATP | SD | ATP | SD |
| saline | 100 | 4 | 100 | 5 | 100 | 6 | 100 | 4 | 100 | 4 | 100 | 11 |
| 2-1 | 85 | 3 | 89 | 6 | 104 | 3 | 92 | 6 | 86 | 2 | 78 | 3 |
| 3-1 | 101 | 1 | 106 | 3 | 101 | 5 | 63 | 2 | 59 | 0 | 56 | 2 |
| 4-1 | 88 | 3 | 95 | 3 | 62 | 2 | 29 | 1 | 30 | 1 | 30 | 1 |

For assessment of the target knock down (PCSK9 mRNA levels) total mRNA was extracted from the cells adding 100 µl of 1× RNA lysis mixture (QuantiGene® Sample Processing Kit, QS0101) directly into the wells according to the manufacturer's instructions. RNA lysis mixtures were kept at −80° C. until analysis. For gene expression analysis, 20 µl of lysates were mixed with an mRNA-capture magnetic beads sets (Panomics QuantiGene® Plex Set catalog #12697), incubated overnight, processed for branched DNA amplification and analyzed according to the manufacturer's instructions (Panomics QuantiGene® Plex Assay kit, QP1015). The PPIB probe was used as housekeeping gene for normalization. Average Fluoresence Intensity (FI) and standard deviation of 3 biological replicates were calculated and normalized on vehicle control. The results are shown in table 11, and represent the average of three identical treatments.

TABLE 11

PCSK9 mRNA as % of saline with varying levels of EGF in the medium

| | EGF ng/ml | | | |
|---|---|---|---|---|
| | 0 | | 10 | |
| Comp # | PCSK9 mRNA | SD | PCSK9 mRNA | SD |
| saline | 100.00 | 0.96 | 100.00 | 0.97 |
| 2-1 | 1.73 | 0.06 | 1.02 | 0.08 |
| 3-1 | 2.28 | 0.18 | 1.46 | 0.10 |
| 4-1 | 6.84 | 0.36 | 1.47 | 0.04 |

These results show that when applying oligonucleotide to PTEC-TERT1 cells the effect on the intracellular ATP levels is dependent on the EGF concentration in the medium, whereas the target knockdown is unaffected by the EGF levels in the medium. At 10 ng/ml of EGF in the medium the toxicity of the oligonucleotide compounds can be differentiated nicely, whereas below 3 ng/ml no significant differentiation can be observed. The need for EGF in the medium is consistent with the findings in example 6 with EGF as a biomarker.

Example 11 Effect on Assay when EGFR is Blocked

The present example set out to identify whether blocking EGFR on the cell line used for the nephrotoxicity assay of the invention affects the assay.

Erlotinib, a small molecule inhibitor of EGFR kinase activity was used in the present assay at 5 µM. Intracellular ATP levels were measured in confluent PTEC-TERT1 after 9 days exposure to 100 µM oligonucleotide along with 10 ng/ml of EGF in the medium with and without erlotinib.

The results are shown in table 12, and represent the average of three identical treatments.

TABLE 12

Effect on intracellular ATP of oligonucleotides in the presence of erlotinib

| | | No erlotinib | | 5 µM erlotinib | |
|---|---|---|---|---|---|
| In vivo grade of toxicity | Comp# | ATP % Saline | SD | ATP % Saline | SD |
| Innocuous | 1-1 | 108.61 | 5.43 | 95.54 | 3.02 |
| low | 2-1 | 107.67 | 2.93 | 84.31 | 1.07 |
| Innocuous | 6-1 | 102.45 | 2.36 | 104.16 | 2.82 |

TABLE 12-continued

Effect on intracellular ATP of oligonucleotides in the presence of erlotinib

| | | No erlotinib | | 5 µM erlotinib | |
|---|---|---|---|---|---|
| In vivo grade of toxicity | Comp# | ATP % Saline | SD | ATP % Saline | SD |
| Medium | 3-1 | 87.67 | 2.19 | 89.59 | 4.74 |
| High | 5-1 | 82.90 | 3.40 | 89.58 | 4.61 |
| High | 4-1 | 65.71 | 3.20 | 94.44 | 4.74 |
| High | 8-1 | 50.28 | 0.20 | 97.47 | 2.46 |

These data show that the ATP profile of innocuous and toxic oligonucleotides was undistinguishable in cells where EGFR was inactivated using erlotinib. This is a strong indication that EGFR expression is need to be functional in cells when assessing the nephrotoxicity profile of oligonucleotides in cell based assays.

Example 12: Oligonucleotide Effects on Intracellular a TP in PTEC-TERT1 Cells

In examples 4, 6, 10 and 11 above ATP has shown to be useful as an alternative or supplementary biomarker to EGF when assessing nephrotoxicity. The conditions need to get an effect on intracellular ATP levels in PTEC-TERT1 cells of compounds 1-1, 3-1 and 4-1 from table 1 were investigated.

The PTEC-TERT1 cells were cultured as described in the "Materials and methods" section. Confluent monolayers of PTEC-TERT1 cells were treated with oligonucleotide as described in the "Materials and methods" section in concentrations of 3, 10, 30 or 100 µM. The treatment was either conducted for 3 days or 9 days.

The results are shown in tables 13 and 14 below, and represents the average of three identical treatments.

TABLE 13

% of ATP following single treatment

| | | | Day 6 | | Day 9 | |
|---|---|---|---|---|---|---|
| In vivo tox | Comp # | Conc µM | ATP % of saline | SD | ATP % of saline | SD |
| Innocuous | 1-1 | 3 | 97.84 | 3.69 | 95.07 | 8.61 |
| | | 10 | 98.29 | 7.24 | 89.96 | 5.41 |
| | | 30 | 99.61 | 6.37 | 94.13 | 8.11 |
| | | 100 | 94.98 | 5.34 | 89.84 | 5.90 |
| Medium | 3-1 | 3 | 114.58 | 6.59 | 100.99 | 9.75 |
| | | 10 | 122.34 | 4.27 | 106.57 | 6.19 |
| | | 30 | 114.36 | 9.85 | 105.09 | 6.39 |
| | | 100 | 105.44 | 9.33 | 89.54 | 4.10 |
| High | 4-1 | 3 | 100.51 | 5.51 | 76.84 | 8.24 |
| | | 10 | 96.60 | 1.58 | 70.64 | 3.24 |
| | | 30 | 83.98 | 2.70 | 54.70 | 5.37 |
| | | 100 | 62.39 | 4.06 | 41.34 | 2.21 |

TABLE 14

% of ATP following 3 times repeated treatment, where each treatment is with the concentration indicated in the table.

| | | | Day 6 | | Day 9 | |
|---|---|---|---|---|---|---|
| In vivo tox | Comp # | Conc µM | ATP % of saline | SD | ATP % of saline | SD |
| Innocuous | 1-1 | 3 | 94.25 | 6.19 | 92.28 | 7.10 |
| | | 10 | 96.43 | 4.32 | 90.75 | 9.78 |

TABLE 14-continued

% of ATP following 3 times repeated treatment, where each treatment is with the concentration indicated in the table.

| | | | Day 6 | | Day 9 | |
|---|---|---|---|---|---|---|
| In vivo tox | Comp # | Conc µM | ATP % of saline | SD | ATP % of saline | SD |
| | | 30 | 98.37 | 5.36 | 90.76 | 7.00 |
| | | 100 | 98.16 | 4.42 | 92.26 | 7.29 |
| Medium | 3-1 | 3 | 112.48 | 2.29 | 106.66 | 5.29 |
| | | 10 | 110.21 | 5.81 | 104.98 | 3.95 |
| | | 30 | 106.47 | 4.19 | 90.28 | 4.45 |
| | | 100 | 96.98 | 3.80 | 43.07 | 7.34 |
| Sever tox | 4-1 | 3 | 87.80 | 4.33 | 77.94 | 2.26 |
| | | 10 | 79.97 | 3.02 | 69.91 | 7.29 |
| | | 30 | 72.33 | 6.41 | 52.34 | 3.72 |
| | | 100 | 54.80 | 0.80 | 38.39 | 2.90 |

From this it can be seen that reduction of intracellular ATP in PTEC-TERT1 cells can be observed for the severely toxic compound 4-1 following single treatment at day 6 and in particular at day 9. Whereas for the medium toxic compound 3-1 effects on intracellular ATP are observed at day 9 for single treatment at the 100 µM dose, and at 30 µM doses for repeated treatment.

Example 13: Oligonucleotide Effects on Intracellular ATP in Primary Human PTEC Cells The ability to differentiate the degree of toxicity between compound 4-1 (high tox) and 3-1 (medium tox), based on an in vitro effect on intracellular ATP levels in human primary PTEC cells and PTEC-TERT1 cells was investigated.

The cells were cultured as described in the "Materials and methods" section. At confluence the cells were treated with oligonucleotide as described in the "Materials and methods" section, in concentrations as indicated in the table below. The treatment was performed for 9 days.

The results are shown in tables 15 below, and represent the average of three identical treatments.

TABLE 15

% of ATP in a dose response

Primary PTEC
Comp #

| | 1-1 | | 3-1 | | 4-1 | |
|---|---|---|---|---|---|---|
| Conc µM | ATP % of saline | SD | ATP % of saline | SD | ATP % of saline | SD |
| 1.23 | 100.00 | 1.78 | 99.57 | 5.03 | 97.45 | 5.80 |
| 3.70 | 101.00 | 2.12 | 103.27 | 4.11 | 98.15 | 2.54 |
| 11.11 | 103.00 | 2.41 | 102.67 | 2.99 | 93.61 | 1.31 |
| 33.33 | 104.00 | 3.53 | 97.93 | 4.45 | 83.48 | 1.35 |
| 100.00 | 104.00 | 1.60 | 73.55 | 4.64 | 50.26 | 2.56 |

PTEC TERT1
Comp #

| | 10 | | 13 | | 12 | |
|---|---|---|---|---|---|---|
| Conc µM | ATP % of saline | SD | ATP % of saline | SD | ATP % of saline | SD |
| 1.23 | 112.76 | 2.66 | 116.23 | 3.07 | 111.97 | 2.09 |
| 3.70 | 112.94 | 4.45 | 117.74 | 4.33 | 108.70 | 2.02 |
| 11.11 | 109.20 | 3.48 | 118.21 | 8.08 | 90.66 | 0.94 |

TABLE 15-continued

% of ATP in a dose response

| 33.33 | 106.04 | 2.37 | 113.08 | 3.44 | 59.22 | 2.78 |
|---|---|---|---|---|---|---|
| 100.00 | 104.83 | 3.56 | 57.12 | 5.20 | 33.18 | 2.17 |

From this it can be seen that both cell lines are capable of differentiating the toxicity between oligonucleotide 3-1 (medium toxic) and oligonucleotide 4-1 (highly toxic), while the non-toxic oligonucleotide 1-1 does not result in a decrease of intracellular ATP.

Example 14: Effects of Cyclosporine A and Staurosporine on EGF Levels in PTEC-TERT1 Cells The present example investigated whether the in vitro nephrotoxicity assay illustrated for oligonucleotides in the above examples also was applicable to other drug compounds with known nephrotoxicity.

Primary PTEC or PTEC-TERT1 cells were cultured as described in the "Materials and methods" section. Confluent monolayers of primary PTEC or PTEC-TERT1 cells were exposed to cyclosporine A (Sigma-Aldrich C3662) or Staurosporine (Sigma-Aldrich S4400) diluted in DMSO and added to the cell culture at a final concentration of 1, 3, 10, 30 or 100 µM in a final volume of 100 µl. The level of EGF in the medium was measured 3 days after the treatment. DMSO served as vehicle control.

The results are shown in tables 16 below, and represent the average of three identical treatments

TABLE 16

EGF levels in cell cultures as % of control treated with cyclosporine A or staurosporine for 3 days

| | Conc | PTEC-TERT1 | | Primary PTEC | |
|---|---|---|---|---|---|
| Compound | µM | EGF % of DMSO | SD | EGF % of DMSO | SD |
| DMSO | — | 100 | 8 | 100 | 10 |
| cyclosporine A | 1 | 357 | 37 | 119 | 10 |
| | 3 | 768 | 15 | 425 | 44 |
| | 10 | 1094 | 184 | 915 | 18 |
| | 30 | 1122 | 172 | 1303 | 220 |
| | 100 | 1543 | 46 | 1335 | 205 |
| staurosporine | 1 | 517 | 57 | 677 | 79 |
| | 3 | 590 | 210 | 549 | 140 |
| | 10 | 428 | 14 | 540 | 71 |
| | 30 | 613 | 162 | 705 | 84 |
| | 100 | 627 | 187 | 1099 | 293 |

From these data it can be seen that the in vivo nephrotoxicity of two very different small molecule drugs, cyclosporine A (immunosuppressant drug) and staurosporine (antibiotic drug), can be reproduced in vitro using the assay of the present invention. The data also indicates that the assay can detect the nephrotoxicity down to 1 µM of these drugs, and maybe even lower.

Example 15: Oligonucleotide Effects on ATP, EGF and Kim-1 in Primary PTEC and PTEC-TERT1 Cells Compound 20-1, is also known as ISIS, 388626 is an antisense oligonucleotide comprising 2'-O-methoxyethyl-RNA (MOE) modifications, targeting sodium-glucose co-transporter 2 (SGLT2). This compound has been shown to cause reversible in vivo nephrotoxicity in humans when dosed weekly at 50 mg, 100 mg or 200 mg in a 13 week study (Meer et al 2016 J Pharmacol Exp Ther Vol 359 pp 280-289).

In the present example it was investigated whether this nephrotoxicity could be predicted by measuring extracellular EGF and KIM-1 and intracellular ATP upon administration of compound 20-1 to primary PTEC cells or PTEC-TERT1 cells.

The primary PTEC cells and immortalized PTEC-TERT-1 cell line were cultured according to the conditions described in the "Materials and methods" section. At confluence the cells were treated with oligonucleotide as described in the "Materials and methods" section, in concentrations of 30, 100, 300, 400 or 500 µM.

The EGF, KIM-1 and ATP biomarkers were measured using the assays described in the "Materials and methods" section.

The results are shown in tables 17 and 18 below and represent the average of three identical treatments.

TABLE 17

EGF and KIM-1 concentrations 6 days after oligonucleotide treatment and ATP concentration after 9 days of treatment in primary PTEC cells

| Conc µM | Day 6 EGF % saline | SD | Day 6 KIM-1 % saline | SD | Day 9 ATP % saline | SD |
|---|---|---|---|---|---|---|
| saline | 100 | 2 | 100 | 13 | 100 | 1 |
| 30 | 338 | 62 | 134 | 13 | 101 | 1 |
| 100 | 2445 | 143 | 157 | 14 | 95 | 5 |
| 300 | 2980 | 1026 | 157 | 8 | 51 | 1 |

TABLE 17-continued

EGF and KIM-1 concentrations 6 days after oligonucleotide treatment and ATP concentration after 9 days of treatment in primary PTEC cells

| Conc µM | Day 6 EGF % saline | SD | Day 6 KIM-1 % saline | SD | Day 9 ATP % saline | SD |
|---|---|---|---|---|---|---|
| 400 | 3484 | 1085 | 147 | 17 | 41 | 3 |
| 500 | 5431 | 1371 | 125 | 9 | 28 | 2 |

TABLE 18

EGF and KIM-1 concentrations 6 days after oligonucleotide treatment and ATP concentration after 9 days of treatment in PTEC-TERT1 cells

| Conc µM | Day 6 EGF % saline | SD | Day 6 KIM-1 % saline | SD | Day 9 ATP % saline | SD |
|---|---|---|---|---|---|---|
| saline | 100 | 6 | 100 | 17 | 100 | 2 |
| 30 | 111 | 8 | 199 | 11 | 104 | 1 |
| 100 | 125 | 10 | 273 | 16 | 102 | 1 |
| 300 | 205 | 9 | 352 | 6 | 106 | 1 |
| 400 | 297 | 13 | 375 | 29 | 101 | 1 |
| 500 | 307 | 42 | 400 | 5 | 102 | 1 |

From these data it can be seen that the in vivo nephrotoxicity of the MOE antisense oligonucleotide (compound 20-1) showing in vivo nephrotoxicity could be predicted using both primary PTEC cells and PTEC-TERT1 cells with EGF as biomarker. ATP reduction was only observed in the primary PTEC cells, whereas predictive KIM-1 elevation only was observed in PTEC-TERT1 cells. Overall, the assay predicted the nephrotoxicity based on EGF, and ATP and KIM-1 supported this prediction depending on the cell line used.

The invention claimed is:

1. An in vitro method for predicting in vivo nephrotoxicity of a drug substance in a mammal, said method comprising the steps of:
   a) culturing cells expressing epidermal growth factor receptor (EGFR) in a suitable cell culture media containing at least 4 ng/ml of epidermal growth factor (EGF);
   b) administering the drug substance to said cell culture;
   c) incubating the cells for a period of time; and
   d) subsequently measuring the EGF level in the supernatant;
   wherein an increase in EGF in the supernatant is indicative of a drug substance which is, or is predicted to be, associated with nephrotoxicity.

2. The method according to claim 1, wherein EGF level in the supernatant is compared to a reference value obtained from cells treated with vehicle control or a non-toxic reference drug substance, where the non-toxic drug substance has been validated as non-toxic in vivo.

3. The method according to claim 2, wherein the non-toxic reference drug substance is an oligonucleotide compound consisting of CGTcagtatgcgAATc (SEQ ID NO: 1), wherein lower case letters represent DNA units, bold upper case letters represent beta-D-oxy-LNA units, all LNA C are 5' methyl C and all internucleoside linkages are phosphorothioate linkage.

4. The method according to claim 3, wherein a level of EGF in the supernatant above 200% relative to the vehicle control or non-toxic reference value is predicative of nephrotoxicity of the drug substance.

5. The method according to claim 1, wherein EGF level in the supernatant is further compared to a second reference value obtained from cells treated with a nephrotoxic drug substance, where the nephrotoxic reference drug substance has been validated to cause nephrotoxicity in vivo.

6. The method according to claim 5, wherein the toxic reference drug substance is an oligonucleotide compound consisting of GCtgtgtgagcttGG (SEQ ID NO: 4), wherein lower case letters represent DNA units, bold upper case letters represent beta-D-oxy-LNA units, all LNA C are 5' methyl C and all internucleoside linkages are phosphorothioate linkage.

7. The method according to claim 1, wherein the EGF level in the supernatant is compared to a reference value obtained from cells treated a non-toxic reference drug substance ("non-toxic reference") and to a value obtained from cells treated with a toxic reference drug substance ("toxic reference") and wherein a toxicity grade is determined according to the following formula:

$$\left( \frac{([EGF] \text{ drug substance} - [EGF] \text{ non-toxic reference} + (AW/100))}{[EGF] \text{ toxic reference} - [EGF] \text{ non-toxic reference} + (AW/100))} \right) \times 100\%$$

wherein AW is the assay window, which is determined as the difference between the non-toxic reference drug substance and the toxic reference drug substance.

8. The method according claim 7, wherein a toxicity grade above 6, 20 or 50 is predictive of nephrotoxicity of the drug substance.

9. The method according to claim 1, wherein step d) further comprises the measurement of intracellular adenosine triphosphate (ATP) levels;
wherein a decrease in intracellular ATP levels is indicative of a drug substance which is, or is predicted to be, associated with nephrotoxicity.

10. The method according to claim 9, wherein a level of intracellular ATP below 80% relative to the saline or non-toxic reference value is predicative of nephrotoxicity of the drug substance.

11. The method according to claim 1, wherein step d) further comprises the measurement of extracellular kidney injury molecule-1 (KIM-1) protein or intracellular mRNA levels, wherein an increase in KIM-1 levels are indicative of a drug substance which is, or is predicted to be, associated with nephrotoxicity.

12. The method according to claim 11, wherein a level of above 200% relative to a saline or non-toxic reference value is predicative of nephrotoxicity of the drug substance.

13. The method according to claim 1, wherein the cells expressing EGFR is selected from the group consisting of epithelial cell, endothelial cell, mesenchymal cells, neuroectodermal cells and hepatocytes.

14. The method according to claim 13, wherein the cell culture is a primary kidney epithelial cell culture selected from the group consisting of proximal tubule epithelial cells (PTEC), distal tubule epithelial cells and collecting duct epithelial cells, said cells comprising primary human PTEC or rat PTEC.

15. The method according to claim 13, wherein the cells expressing EGFR are cultured from an immortalized cell line selected from the group consisting of recombinant renal proximal tubule cells/TERT-immortalized-1 (PTEC-TERT-1), conditionally immortalized renal proximal tubule cells (ciPTEC-TERT-1), human kidney 2 (HK-2), Nederlands Kanker Instituut-2 (Nki-2) and human A549.

16. The method according claim 1, wherein the period of incubation with the drug substance is between 2 and 6 days.

17. The method according to claim 1, wherein the drug substance is selected from the group consisting of: nucleic acid based molecules, chemotherapeutic agents; aminoglycosides; anti-bacterial agents, anti-viral agents;
anti-fungal agents, anti-inflammatory agents and immunosuppressant agents.

18. The method according to claim 1, wherein the drug substance is a nucleic acid molecule selected from the group consisting of: an RNAi molecule, an antisense oligonucleotide and an aptamer.

19. The method according to claim 18, wherein the nucleic acid molecule comprises one or more 2' sugar modified nucleosides, independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

20. The method according to claim 18, wherein the nucleic acid molecule comprises at least one modified internucleoside linkage.

21. The method according to claim 11, wherein the increase in KIM-1 is predicative of nephrotoxicity for a nucleic acid molecule even if the EGF levels are not increased.

* * * * *